United States Patent [19]

Kawamoto et al.

[11] 4,421,758
[45] Dec. 20, 1983

[54] ANTI-MICROBIAL DIAZOLE DERIVATIVES

[75] Inventors: Isao Kawamoto; Masaki Nakahara, both of Hiromachi, Japan

[73] Assignee: Sankyo Company Limited, Tokyo, Japan

[21] Appl. No.: 329,995

[22] Filed: Dec. 11, 1981

[30] Foreign Application Priority Data

Dec. 12, 1980 [JP] Japan .................................. 55-175525
Feb. 3, 1981 [JP] Japan .................................. 56-14771

[51] Int. Cl.³ .................. A01N 43/50; A61K 31/415; C07D 405/06
[52] U.S. Cl. ................ 424/273 R; 424/269; 544/366; 544/370; 548/262; 548/336; 549/416
[58] Field of Search ..................... 548/336; 424/273 R

[56] References Cited

U.S. PATENT DOCUMENTS 4,313,953  2/1982  Heeres et al. ................... 548/336 X

FOREIGN PATENT DOCUMENTS 2027701  2/1980  United Kingdom ................ 548/336

Primary Examiner—Richard A. Schwartz
Attorney, Agent, or Firm—Frishauf, Holtz, Goodman & Woodward

[57] ABSTRACT

Compounds of formula (I):

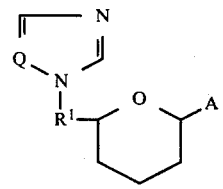

[wherein:
Q represents a =CH— group or a nitrogen atom;
$R^1$ represents a methylene group, a group of formula $$-CH_2CH(R^3)-OCH_2-$$

($R^3$ being a substituted or unsubstituted phenyl group) or a group of formula $$-(CH_2)_n-CH(R^4)-O-$$

(n being 1 or 2 and $R^4$ being a substituted or unsubstituted phenyl or phenylalkyl group); and
A represents a group of formula $$-OR^2$$

($R^2$ being an alkenyl group, an alkynyl group or a substituted or unsubstituted alkyl or phenyl group) or a group of formula $$-CH_2-XR^{11}$$

(X being an oxygen or sulphur atom and $R^{11}$ being an aryl or aralkyl group or, when X represents an oxygen atom, $R^{11}$ being a hydrogen atom or a carbonyloxy or sulphonyloxy group) and
acid addition salts and metal complexes thereof are valuable antimicrobial agents having low toxicity to humans and other animals and are especially valuable for the eradication of fungi.

24 Claims, No Drawings

ANTI-MICROBIAL DIAZOLE DERIVATIVES

BACKGROUND TO THE INVENTION

The present invention relates to a series of new diazole and triazole compounds containing a tetrahydropyranyl substituent, to processes for preparing these compounds and to antimicrobial compositions containing them.

Although many antimicrobial agents are known, their spectrum of activity is generally restricted. Thus, whilst many antibiotics are known which are effective against a limited class of bacteria, often these compounds are ineffective or of very limited effect against other bacteria and they are often totally ineffective against fungi and protozoa. Other compounds, which may be effective against fungi or protozoa, are often only effective against a limited class of such microorganisms, and fungi, in particular, are very difficult to eradicate. Moreover, many compounds which are considered to have good antimicrobial activity turn out to be of no practical value because they have too high a toxicity to humans or to other animals. Accordingly, there is a continuing demand for new antimicrobial agents, particularly for such agents which are effective against fungi.

E. F. Godefroi et al. [J. Med. Chem. 12, 784 (1969)] disclose that a variety of ether-type derivatives of α-phenylimidazole-1-ethanol and cyclic ketal derivatives of 2-(1-imidazolyl)acetophenones have some antimycotic activity, as well as activity against certain gram-positive and gram-negative bacteria.

BRIEF SUMMARY OF INVENTION

The present invention provides a series of new compounds of formula (I):

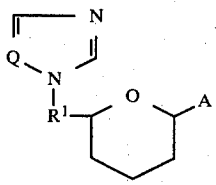

wherein:
Q represents a =CH— group or a nitrogen atom;
$R^1$ represents a methylene group, a group of formula

—CH$_2$CH(R$^3$)—OCH$_2$—

(in which $R^3$ represents a substituted or unsubstituted phenyl group) or a group of formula —(CH$_2$)$_n$—CH(R$^4$)—O—

(in which n is 1 or 2 and $R^4$ represents a substituted or unsubstituted phenyl group or a substituted or unsubstituted phenylalkyl group); and
A represents a group of formula

—OR$^2$ (in which $R^2$ represents an alkyl group, an alkenyl group, an alkynyl group, a substituted or unsubstituted phenyl group or a group of formula

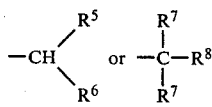

in which $R^5$ represents a hydrogen atom, an alkyl group, a substituted or unsubstituted phenyl group, a substituted or unsubstituted thienyl group or a substituted or unsubstituted furyl group, $R^6$ represents a substituted or unsubstituted phenyl group, a substituted or unsubstituted benzyl group, a substituted or unsubstituted thienyl group or a substituted or unsubstituted furyl group, $R^7$ represents an alkyl group, the two groups $R^7$ being the same or different, and $R^8$ represents a substituted or unsubstituted phenyl group)
or a group of formula

—CH$_2$—XR$^{11}$

[in which X represents an oxygen atom or a sulphur atom and $R^{11}$ represents a naphthyl group, a substituted or unsubstituted phenyl group or a substituted or unsubstituted benzyl group; or, when X represents an oxygen atom, $R^{11}$ represents a hydrogen atom, a group of formula

(in which $R^{10}$ represents an alkyl group, a substituted or unsubstituted phenyl group or a substituted amino group) or a group of formula

—SO$_2$R$^9$ (in which $R^9$ represents an alkyl or aryl group)].

The invention also provides acid addition salts and metal complexes of the compounds of formula (I).

The invention still further provides processes for the preparation of these compounds and a pharmaceutical composition comprising an antimicrobial agent and a pharmaceutically acceptable carrier or diluent, wherein the antimicrobial agent comprises at least one compound of formula (I) or an acid addition salt or metal complex thereof.

DETAILED DESCRIPTION OF INVENTION

A preferred class of compounds of the present invention are those compounds of formula (II):

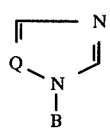

in which B represents a group of formula

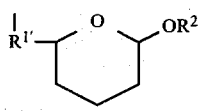

[in which R$^{1'}$ represents a methylene group or a group of formula —CH$_2$CH(R$^3$)—OCH$_2$—] or a group of formula

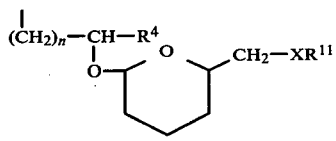

(in which n, X, R$^4$ and R$^{11}$ are as defined above), that is to say compounds of formula (IIa):

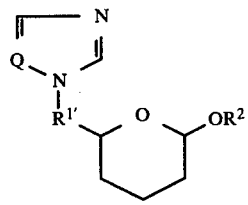
(IIa)

(in which Q, R$^1$ and R$^2$ are as defined above) and compounds of formula (IIb):

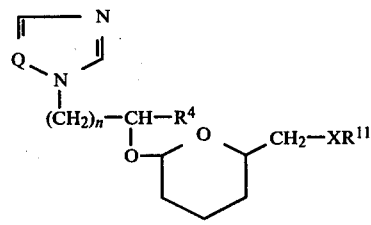
(IIb)

(in which Q, n, X, R$^4$ and R$^{11}$ are as defined above).

Of the compounds of formula (IIa), we prefer those in which:

Q represents a =CH— group or a nitrogen atom;
R$^{1'}$ represents a methylene group or a group of formula

—CH$_2$CH(R$^3$)—OCH$_2$—

(in which R$^3$ represents a phenyl group or a substituted phenyl group having one or two halogen, lower alkyl or lower alkoxy substituents); and R$^2$ represents a lower alkyl group, a lower alkenyl group, a lower alkynyl group, a phenyl group, a substituted phenyl group having from 1 to 3 halogen, lower alkyl or alkoxy substituents or a group of formula

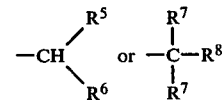

(in which:
R$^5$ represents a hydrogen atom, a lower alkyl group, a phenyl group, a substituted phenyl group having one or two halogen, lower alkyl or lower alkoxy substituents, a thienyl group, a substituted thienyl group having one halogen substituent, a furyl group or a substituted furyl group having one halogen substituent;
R$^6$ represents a phenyl group, a substituted phenyl group having from 1 to 3 halogen, lower alkyl, lower alkoxy, nitro, phenoxy or phenyl substituents, a benzyl group, a substituted benzyl group having one or two halogen, lower alkyl or lower alkoxy substituents on the benzene ring, a thienyl group, a substituted thienyl group having one halogen substituent, a furyl group or a substituted furyl group having one halogen substituent;
R$^7$ represents a lower alkyl group; and
R$^8$ represents a phenyl group or a substituted phenyl group having one or two halogen, lower alkyl or lower alkoxy substituents).

The more preferred compounds of formula (IIa) are those in which R$^2$ represents a group of formula

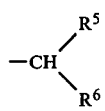

(in which R$^5$ and R$^6$ are as defined above). In particular, we prefer those compounds in which R$^5$ represents a hydrogen atom, a lower alkyl group, a phenyl group, a substituted phenyl group having one or two halogen substituents, a thienyl group or a substituted thienyl group having one halogen substituent and R$^6$ represents a phenyl group, a substituted phenyl group having one or two halogen substituents, a benzyl group or a substituted benzyl group having one or two halogen substituents; in this case, when R$^{1'}$ represents a group of formula —CH$_2$CH(R$^3$)—OCH$_2$—, R$^3$ preferably represents a phenyl group or a substituted phenyl group having one or two halogen substituents.

In these more preferred compounds, when R$^{1'}$ represents a methylene group, the most preferred compounds are those in which R$^5$ represents a hydrogen atom, a phenyl group or a substituted phenyl group having one or two halogen substituents and R$^6$ represents a phenyl group or a substituted phenyl group having one or two halogen substituents, or those compounds in which R$^5$ represents a phenyl group, a thienyl group, a substituted phenyl group having one or two halogen substituents or a substituted thienyl group having one halogen substituent and R$^6$ represents a benzyl group or a substituted benzyl group having one or two halogen substituents.

Of the more preferred compounds mentioned above, when R$^{1'}$ represents a group of formula —CH$_2$CH(R$^3$)—OCH$_2$—, the most preferred compounds are those in which R$^3$ represents a phenyl group or a substituted phenyl group having one or two halogen substituents, R$^5$ represents a hydrogen atom and R$^6$ represents a phenyl group or a substituted phenyl group having one or two halogen substituents.

Of the compounds of formula (IIb), those compounds are preferred in which:
Q represents a =CH— group or a nitrogen atom;
n represents 1 or 2;
R$^4$ represents, when n is 1, a substituted or unsubstituted phenyl group or a substituted or unsubstituted phenylalkyl group or, when n is 2, a substituted or unsubstituted phenyl group, the substituents being on the benzene ring of the phenyl or phenylalkyl group and being one or two halogen atoms, lower alkyl groups or lower alkoxy groups;
X represents an oxygen atom or a sulphur atom; and
R$^{11}$ represents a naphthyl group, a phenyl group, a substituted phenyl group having from 1 to 3 substituents [wherein the substituents are selected from halogen atoms, lower alkyl groups, lower alkoxy groups, phenyl groups, lower alkanoylamino groups, groups of formula

(in which R$^{12}$ represents a hydrogen atom, a phenyl group or a lower alkyl group) and groups of formula

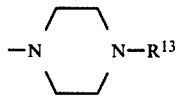

(in which R$^{13}$ represents a hydrogen atom, a lower alkyl group, a lower alkanoyl group or a benzoyl group)], a benzyl group, a substituted benzyl group having on the benzene ring from 1 to 3 substituents [wherein the substituents are selected from halogen atoms, lower alkyl groups, lower alkoxy groups and groups of formula

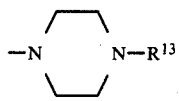

(in which R$^{13}$ is as defined above)], or, when X represents an oxygen atom, R$^{11}$ represents a hydrogen atom, a group of formula

(in which R$^{10}$ represents a lower alkyl group, a phenyl group, a substituted phenyl group or a substituted amino group) or a group of formula

(in which R$^9$ represents a lower alkyl group or an aryl group).

The more preferred compounds of formula (IIb) are those in which X represents an oxygen atom and R$^{11}$ represents a hydrogen atom or those in which:

X represents an oxygen atom or a sulphur atom; and
R$^{11}$ represents a naphthyl group, a phenyl group, a substituted phenyl group having from 1 to 3 substituents [wherein the substituents are selected from halogen atoms, lower alkoxy groups, phenyl groups, lower alkanoylamino groups, groups of formula —CONHR$^{12}$ (in which R$^{12}$ represents a hydrogen atom, a phenyl group or a lower alkyl group) and groups of formula

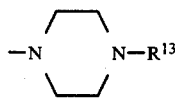

(in which R$^{13}$ represents a hydrogen atom, a lower alkyl group, a lower alkanoyl group or a benzoyl group)], a benzyl group or a substituted benzyl group having on the benzene ring from 1 to 3 substituents [wherein the substituents are selected from halogen atoms, lower alkyl groups, lower alkoxy groups and groups of formula

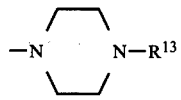

(in which R$^{13}$ is as defined above).

A still more preferred class of compound of formula (IIb) are those compounds in which:

Q represents a =CH— group;
n is 1;
X represents an oxygen atom or a sulphur atom;
R$^4$ represents a phenyl group, a substituted phenyl group having one or two halogen substituents, a phenethyl group or a substituted phenethyl group having one or two halogen substituents on the benzene ring; and
R$^{11}$ represents a phenyl group having, at the p-position, a halogen, lower alkanoylamino, phenyl or

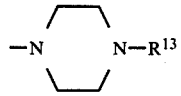

(in which R$^{13}$ represents a lower alkyl group, a lower alkanoyl group or a benzoyl group) substituent and optionally having one further halogen substituent, or a benzyl group which has, at the p-position of the benzene ring, a halogen or

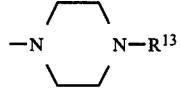

(in which R$^{13}$ is as defined above) substituent and optionally having one further halogen substituent.

The most preferred compounds of formula (IIb) are those in which:

X represents an oxygen atom;
R$^4$ represents a phenyl group having one or two halogen substituents; and
R$^{11}$ represents a 4-halo-, 2,4-dihalo- or 4-phenyl-substituted phenyl group, a 4-halo- or 2,4-dihalo-substituted benzyl group, a phenyl group, a benzyl group or a phenyl or benzyl group having a substituent selected from a halogen atom at the 2-position and a group of formula

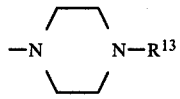

(in which R$^{13}$ represents an acetyl group or a benzoyl group) at the 4-position. In particular, we prefer those compounds in which R$^4$ represents a 2,4-dichlorophenyl group.

In all of the compounds of the invention, including the preferred compounds mentioned above, we particularly prefer those compounds in which Q represents a =CH— group, that is to say imidazole derivatives.

The compounds of the invention exist in the form of cis and trans stereoisomers with respect to the 2- and 6-positions of the tetrahydropyran ring and the separate isomers or mixtures thereof may be prepared, as is well known in the art, by appropriate choice of starting materials. The present invention embraces both the individual isomers and mixtures thereof.

Moreover, the compounds of the invention can provide a large number of optical isomers because of the many asymmetric carbon atoms in the compounds. Thus, the carbon atoms of the 2- and 6-positions of the tetrahydropyran ring are asymmetric, as also, when $R^1$ represents a group of formula $-CH_2CH(R^3)-OCH_2-$ or $-(CH_2)_n-CH(R^4)-O-$, are the carbon atoms to which the groups represented by $R^3$ and $R^4$ are attached. The central carbon atom of the group of formula

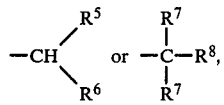

which may be represented by $R^2$, is also asymmetric when $R^5$ and $R^6$ or the two groups represented by $R^7$ are different. Optical isomers can exist for each of these asymmetric carbon atoms and the present invention embraces both the individual isomers as well as mixtures thereof. These optical isomers are usually obtained as racemic mixtures. In the present specification, the stereoisomers based on the asymmetric carbon atom of the compound of formula

which may be represented by $R^2$, or on the asymmetric carbon atom of the group of formula $-(CH_2)_n-CH(R^4)-O-$, which may be represented by $R^1$, where they are separated but are not otherwise identified, are referred to as the isomers of "greater polarity" or of "lesser polarity". The optical isomers of these compounds can, if desired, be resolved by separating the compounds of the invention or intermediate compounds in the preparation of the compounds of the invention, by resolution methods well-known in the art, for example by the formation of diastereomeric salts, which are then separated by taking advantage of differences in their physical properties and which are then converted back to the free bases.

In the present specification, the term "lower alkyl" means an alkyl group having up to 6 carbon atoms and the terms "lower alkoxy", "lower alkenyl", "lower alkynyl", "lower alkanoylamino" and "lower alkanoyl" should be construed accordingly as meaning such groups having up to 6 carbon atoms.

In the compounds of formula (I), the lower alkyl groups which may be represented by $R^2$, $R^5$, $R^7$, $R^{12}$ and $R^{13}$, as well as the lower alkyl groups which may be substituents on the phenyl or phenylalkyl (e.g. benzyl) groups represented by $R^2$, $R^3$, $R^4$, $R^6$, $R^8$ and $R^{11}$ may be straight or branched chain alkyl groups and preferably have from 1 to 4 carbon atoms. Examples of such groups include the methyl, ethyl, propyl, isopropyl, butyl, isobutyl and t-butyl groups, preferably the methyl group.

The lower alkenyl group, which may be represented by $R^2$ in the compounds of formula (I) may be a straight or branched chain alkenyl group and is preferably such a group having from 3 to 6 carbon atoms, for example an allyl, 2-butenyl, 2-pentenyl or 2-hexenyl group, preferably an allyl group.

The lower alkynyl group, which may be represented by $R^2$ in the compounds of formula (I) may be a straight or branched chain alkynyl group and is preferably such a group having from 3 to 6 carbon atoms, for example a propargyl, 2-butynyl, 2-pentynyl or 2-hexynyl group, preferably a propargyl group.

The lower alkoxy group, which may be a substituent on the phenyl or phenylalkyl (including benzyl) groups represented by $R^2$, $R^3$, $R^4$, $R^5$, $R^6$, $R^8$ and $R^{11}$ may be a straight or branched chain group and is preferably such a group having from 1 to 4 carbon atoms, for example a methoxy, ethoxy, propoxy or isopropoxy group, preferably a methoxy group.

The lower alkanoyl group, which may be represented by $R^{13}$ in the compounds of formula (I), as well as the lower alkanoyl group forming part of the lower alkanoylamino group, which may be a substituent on the phenyl group represented by $R^{11}$, is preferably such a group having from 1 to 4 carbon atoms, more preferably an acetyl group.

The phenylalkyl group represented by $R^4$ in the compounds of formula (I) and of formula (IIb), is preferably a benzyl or phenethyl group, more preferably a phenethyl group, which may be unsubstituted or may be substituted as defined above with those substituents exemplified above.

The halogen atoms which may be substituents on the phenyl, phenylalkyl (including benzyl), thienyl or furyl groups represented by $R^2$, $R^3$, $R^4$, $R^5$, $R^6$, $R^8$ and $R^{11}$, include chlorine, bromine, fluorine and iodine, preferably, in the case of $R^2$, $R^3$, $R^5$, $R^6$ and $R^8$, chlorine or bromine, most preferably chlorine, and preferably, in the case of $R^4$ and $R^{11}$, chlorine or fluorine.

Most of the free bases represented by formula (I) are oily substances and it is, therefore, often convenient to separate and/or to use them in the form of acid addition salts or metal complexes, which may be prepared by conventional procedures. The nature of these acid addition salts and metal complexes is not critical to the present invention, provided that they retain the antimicrobial activities of the free bases represented by formula (I) and that they are biologically acceptable.

Acid addition salts can be formed from inorganic acids (such as hydrochloric acid, hydrobromic acid, sulphuric acid, nitric acid or phosphoric acid) or organic acids (such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulphonic acid, ethanesulphonic acid or p-toluenesulphonic acid). Preferred acids are hydrochloric acid, nitric acid, oxalic acid, p-toluenesulphonic acid and fumaric acid.

Metal complexes can be formed with cupric chloride, zinc chloride and stannous chloride; however, we particularly prefer the complex salts formed with zinc chloride.

Representative examples of the compounds of the invention are given in the following list; as explained above, these compounds may exist in the form of trans and cis isomers with respect to the 2- and 6-positions of the tetrahydropyranyl ring as well as various optical isomers—the individual isomers and mixtures thereof are included:

1. 1-(6-t-butoxytetrahydropyran-2-ylmethyl)imidazole
2. 1-(6-propargyloxytetrahydropyran-2-ylmethyl)imidazole
3. 1-(6-phenoxytetrahydropyran-2-ylmethyl)imidazole
4. 1-[6-(2,4-dichlorophenoxy)tetrahydropyran-2-ylmethyl]imidazole
5. 1-[6-(4-chloro-2-methylphenoxy)tetrahydropyran-2-ylmethyl]imidazole
6. 1-(6-benzyloxytetrahydropyran-2-ylmethyl)imidazole
7. 1-[6-(4-chlorobenzyloxy)tetrahydropyran-2-ylmethyl]imidazole
8. 1-[6-(2,4-dichlorobenzyloxy)tetrahydropyran-2-ylmethyl]imidazole
9. 1-[6-(2,4-dichlorobenzyloxy)tetrahydropyran-2-ylmethyl]-1H-1,2,4-triazole
10. 1-[6-(2,6-dichlorobenzyloxy)tetrahydropyran-2-ylmethyl]imidazole
11. 1-[6-(2,6-dichlorobenzyloxy)tetrahydropyran-2-ylmethyl]-1H-1,2,4-triazole
12. 1-[6-(5-bromo-2-chlorobenzyloxy)tetrahydropyran-2-ylmethyl]imidazole
13. 1-[6-(2,4-dimethylbenzyloxy)tetrahydropyran-2-ylmethyl]imidazole
14. 1-[6-(2,4-dimethoxybenzyloxy)tetrahydropyran-2-ylmethyl]imidazole
15. 1-[6-(3,4,5-trimethoxybenzyloxy)tetrahydropyran-2-ylmethyl]imidazole
16. 1-[6-(o-phenoxybenzyloxy)tetrahydropyran-2-ylmethyl]imidazole
17. 1-[6-(m-phenoxybenzyloxy)tetrahydropyran-2-ylmethyl]imidazole
18. 1-[6-(p-phenylbenzyloxy)tetrahydropyran-2-ylmethyl]imidazole
19. 1-[6-(2-thienylmethoxy)tetrahydropyran-2-ylmethyl]imidazole
20. 1-(6-furfuryloxytetrahydropyran-2-ylmethyl)imidazole
21. 1-[6-(1-p'-chlorophenylethoxy)tetrahydropyran-2-ylmethyl]imidazole
22. 1-[6-(1-p'-chlorophenylethoxy)tetrahydropyran-2-ylmethyl]-1H-1,2,4-triazole
23. 1-{6-[1-(5-bromo-2-thienyl)ethoxy]tetrahydropyran-2-ylmethyl}imidazole
24. 1-{6-[1-(5-bromo-2-furyl)ethoxy]tetrahydropyran-2-ylmethyl}imidazole
25. 1-{6-[α-(4-chlorophenyl)-2,4-dichlorobenzyloxy]tetrahydropyran-2-ylmethyl}imidazole
26. 1-{6-[α-(4-fluorophenyl)-2,4-dichlorobenzyloxy]tetrahydropyran-2-ylmethyl}imidazole
27. 1-{6-[α-(2-nitrophenyl)-4-chlorobenzyloxy]tetrahydropyran-2-ylmethyl}imidazole
28. 1-{6-[α-(2-thienyl)-4-chlorobenzyloxy]tetrahydropyran-2-ylmethyl}imidazole
29. 1-{6-[α-(2-furyl)-4-fluorobenzyloxy]tetrahydropyran-2-ylmethyl}imidazole
30. 1-(6-phenethyloxytetrahydropyran-2-ylmethyl)imidazole
31. 1-[6-(4-chlorophenethyloxy)tetrahydropyran-2-ylmethyl]imidazole
32. 1-[6-(4-chlorophenethyloxy)tetrahydropyran-2-ylmethyl]-1H-1,2,4-triazole
33. 1-[6-(4-methoxyphenethyloxy)tetrahydropyran-2-ylmethyl]imidazole
34. 1-[6-(2,4-dimethoxyphenethyloxy)tetrahydropyran-2-ylmethyl]imidazole
35. 1-[6-(α-methyl-2,4-dichlorophenethyloxy)tetrahydropyran-2-ylmethyl]imidazole
36. 1-[6-(α-propyl-2,4-dichlorophenethyloxy)tetrahydropyran-2-ylmethyl]imidazole
37. 1-[6-(α-benzyl-2,4-dichlorobenzyloxy)tetrahydropyran-2-ylmethyl]imidazole
38. 1-{6-[α-(4-fluorobenzyl)-4-chlorobenzyloxy]tetrahydropyran-2-ylmethyl}imidazole
39. 1-{6-[α-(4-fluorobenzyl)-4-chlorobenzyloxy]tetrahydropyran-2-ylmethyl}-1H-1,2,4-triazole
40. 1-{6-[α-(4-chlorobenzyl)-2,4-dichlorobenzyloxy]tetrahydropyran-2-ylmethyl}imidazole
41. 1-{6-[α-(4-fluorobenzyl)-2,4-dichlorobenzyloxy]tetrahydropyran-2-ylmethyl}imidazole
42. 1-{6-[α-(4-fluorobenzyl)-2,6-dichlorobenzyloxy]tetrahydropyran-2-ylmethyl}imidazole
43. 1-{6-[α-(2,4-dichlorobenzyl)benzyloxy]tetrahydropyran-2-ylmethyl}imidazole
44. 1-{6-[α-(2,4-dichlorobenzyl)-4-chlorobenzyloxy]tetrahydropyran-2-ylmethyl}imidazole
45. 1-{6-[α-(2,4-dichlorobenzyl)-4-fluorobenzyloxy]tetrahydropyran-2-ylmethyl}imidazole
46. 1-{6-[α-(2,4-dichlorobenzyl)-2,4-dichlorobenzyloxy]tetrahydropyran-2-ylmethyl}imidazole
47. 1-{6-[α-(2,4-dichlorobenzyl)-2,6-dichlorobenzyloxy]tetrahydropyran-2-ylmethyl}imidazole
48. 1-{6-[α-(2,6-dichlorobenzyl)-2,4-dichlorobenzyl)-2,4-dichlorobenzyloxy]tetrahydropyran-2-ylmethyl}imidazole
49. 1-{6-[E-(2,4-dichlorobenzyl)-2-methoxybenzyloxy]tetrahydropyran-2-ylmethyl}imidazole
50. 1-{6-[α-(2,4-dichlorobenzyl)-4-methoxybenzyloxy]tetrahydropyran-2-ylmethyl}imidazole
51. 1-{6-[α-(2,4-dichlorobenzyl)-4-methoxybenzyloxy]tetrahydropyran-2-ylmethyl}-1H-1,2,4-triazole
52. 1-{6-[α-(2,4-dichlorobenzyl)-2,4-dimethylbenzyloxy]tetrahydropyran-2-ylmethyl}imidazole
53. 1-[6-(α-p'-methylbenzyl-2,4-dichlorobenzyloxy)tetrahydropyran-2-ylmethyl]imidazole
54. 1-[6-(α-p'-methoxybenzyl-2,4-dichlorobenzyloxy)tetrahydropyran-2-ylmethyl]imidazole
55. 1-[6-(2,4-dichloro-α-2'-thienylphenethyloxy)tetrahydropyran-2-ylmethyl]imidazole
56. 1-[6-(2,4-dichloro-α-2'-furylphenethyloxy)tetrahydropyran-2-ylmethyl]imidazole
57. 1-{6-[α-(5-bromo-2-furyl)-2,4-dichlorophenethyloxy]tetrahydropyran-2-ylmethyl}imidazole
58. 1-[6-(2,4-dichloro-α,α-dimethylbenzyloxy)tetrahydropyran-2-ylmethyl]imidazole
59. 1-[6-(2,4-dichloro-α,α-dimethylbenzyloxy)tetrahydropyran-2-ylmethyl]-1H-1,2,4-triazole
60. 1-{β-[6-(2,4-dichlorophenoxy)tetrahydropyran-2-ylmethoxy]phenethyl}imidazole
61. 1-{β-[6-(2,4-dichlorobenzyloxy)tetrahydropyran-2-ylmethoxy]phenethyl}imidazole
62. 1-{β-[6-(2,4-dichlorobenzyloxy)tetrahydropyran-2-ylmethoxy]phenethyl}-1H-1,2,4-triazole
63. 1-{β-[6-(2,4-dichlorobenzyloxy)tetrahydropyran-2-ylmethoxy]-4-chlorophenethyl}imidazole
64. 1-{β-[6-(2,4-dichlorobenzyloxy)tetrahydropyran-2-ylmethoxy]-4-chlorophenethyl}-1H-1,2,4-triazole
65. 1-{β-[6-(2,6-dichlorobenzyloxy)tetrahydropyran-2-ylmethoxy]-4-chlorophenethyl}imidazole
66. 1-{β-[6-(4-chlorophenethyloxy)tetrahydropyran-2-ylmethoxy]-4-bromophenethyl}imidazole
67. 1-[β-(6-allyloxytetrahydropyran-2-ylmethoxy)-2,4-dichlorophenethyl]imidazole 68. 1-{β-[6-(4-chloro-2-methylphenoxy)tetrahydropyran-2-ylmethoxy]-2,4-dichlorophenethyl}imidazole
69. 1-{β-[6-(2,4,6-trichlorophenoxy)tetrahydropyran-2-ylmethoxy]-2,4-dichlorophenethyl}imidazole
70. 1-{β-[6-(4-chlorobenzyloxy)tetrahydropyran-2-ylmethoxy]-2,4-dichlorophenethyl}imidazole
71. 1-{β-[6-(4-bromobenzyloxy)tetrahydropyran-2-ylmethoxy]-2,4-dichlorophenethyl}imidazole
72. 1-{β-[6-(2,4-dichlorobenzyloxy)tetrahydropyran-2-ylmethoxy]-2,4-dichlorophenethyl}imidazole
73. 1-{β-[6-(2,4-dichlorobenzyloxy)tetrahydropyran-2-ylmethoxy]-2,4-dichlorophenethyl}-1H-1,2,4-triazole
74. 1-{β-[6-(2,6-dichlorobenzyloxy)tetrahydropyran-2-ylmethoxy]-2,4-dichlorophenethyl}imidazole
75. 1-{β-[6-(2,4-dimethylbenzyloxy)tetrahydropyran-2-ylmethoxy]-2,4-dichlorophenethyl}imidazole
76. 1-{β-[6-(2,4-dimethoxybenzyloxy)tetrahydropyran-2-ylmethoxy]-2,4-dichlorophenethyl}imidazole
77. 1-{β-(α-methyl-2,4-dichlorobenzyloxy)tetrahydropyran-2-ylmethoxy]-2,4-dichlorophenethyl}-imidazole
78. 1-{β-[6-(α-p'-fluorophenyl-2,4-dichlorobenzyloxy)-tetrahydropyran-2-ylmethoxy]-2,4-dichlorophenethyl}imidazole
79. 1-{β-[6-(2,4-dichloro-α,α-dimethylbenzyloxy)tetrahydropyran-2-ylmethoxy]-2,4-dichlorophenethyl}-imidazole
80. 1-{β-[6-(4-chlorophenethyloxy)tetrahydropyran-2-ylmethoxy]-2,4-dichlorophenethyl}imidazole
81. 1-{β-[6-(2,4-dichloro-α-methylphenethyloxy)tetrahydropyran-2-ylmethoxy]-2,4-dichlorophenethyl}-imidazole
82. 1-{β-[6-(α-2',4'-dichlorobenzylbenzyloxy)tetrahydropyran-2-ylmethoxy]-2,4-dichlorophenethyl}-imidazole 83. 1-{β-[6-(α-2'-thienyl-2,4-dichlorophenethyloxy)tetrahydropyran-2-ylmethoxy]-2,4-dichlorophenethyl}imidazole
84. 1-{β-[6-(2,4-dichlorobenzyloxy)tetrahydropyran-2-ylmethoxy]-4-methylphenethyl}imidazole
85. 1-{β-[6-(2,4-dichlorobenzyloxy)tetrahydropyran-2-ylmethoxy]-4-methoxyphenethyl}imidazole
86. 1-{β-[6-(2,4-dichlorophenoxymethyl)tetrahydropyran-2-yloxy]phenethyl}imidazole
87. 1-{β-[6-(2,4-dichlorophenoxymethyl)tetrahydropyran-2-yloxy]-4-chlorophenethyl}imidazole
88. 1-{β-[6-(4-fluorophenoxymethyl)tetrahydropyran-2-yloxy]-4-chlorophenethyl}imidazole
89. 1-{β-[6-(4-acetamidophenoxymethyl)tetrahydropyran-2-yloxy]-4-chlorophenethyl}imidazole
90. 1-{β-[6-(2,4-dichlorophenoxymethyl)tetrahydropyran-2-yloxy]-4-bromophenethyl}imidazole
91. 1-[β-(6-phenoxymethyltetrahydropyran-2-yloxy)-2,4-dichlorophenethyl]imidazole
92. 1-{β-[6-(2-chlorophenoxymethyl)tetrahydropyran-2-yloxy]-2,4-dichlorophenethyl}imidazole
93. 1-{β-[6-(4-chlorophenoxymethyl)tetrahydropyran-2-yloxy]-2,4-dichlorophenethyl}imidazole
94. 1-{β-[6-(4-chlorophenylthiomethyl)tetrahydropyran-2-yloxy]-2,4-dichlorophenethyl}imidazole
95. 1-{β-[6-(4-fluorophenoxymethyl)tetrahydropyran-2-yloxy]-2,4-dichlorophenethyl}imidazole
96. 1-{β-[6-(4-fluorophenoxymethyl)tetrahydropyran-2-yloxy]-2,4-dichlorophenethyl}-1H-1,2,4-triazole
97. 1-{β-[6-(2,4-dichlorophenoxymethyl)tetrahydropyran-2-yloxy]-2,4-dichlorophenethyl}imidazole
98. 1-{β-[6-(2,6p-dichlorophenoxymethyl)tetrahydropyran-2-yloxy]-2,4-dichlorophenethyl}imidazole
99. 1-{β-[6-(4-chloro-2-methylphenoxymethyl)tetrahydropyran-2-yloxy]-2,4-dichlorophenethyl}imidazole
100. 1-{β-[6-(4-chloro-2-methylphenoxymethyl)tetrahydropyran-2-yloxy]-2,4-dichlorophenethyl}-1H-1,2,4-triazole
101. 1-{β-[6-(4-chloro-2-methoxyphenoxymethyl)tetrahydropyran-2-yloxy]-2,4-dichlorophenethyl}-imidazole
102. 1-{β-[6-(2,6-dimethoxyphenoxymethyl)tetrahydropyran-2-yloxy]-2,4-dichlorophenethyl}imidazole
103. 1-[β-(6-p'-biphenylyloxymethyltetrahydropyran-2-yloxy)-2,4-dichlorophenethyl]imidazole
104. 1-[β-(6-p'-biphenylyloxymethyltetrahydropyran-2-yloxy)-2,4-dichlorophenethyl]-1H-1,2,4-triazole
105. 1-{β-[6-(4-acetamidophenoxymethyl)tetrahydropyran-2-yloxy]-2,4-dichlorophenethyl}imidazole
106. 1-{β-[6-(2,6-dichloro-4-acetamidophenoxymethyl)tetrahydropyran-2-yloxy]-2,4-dichlorophenethyl}imidazole
107. 1-{β-[6-(4-carbamoylphenoxymethyl)tetrahydropyran-2-yloxy]-2,4-dichlorophenethyl}imidazole
108. 1-{β-[6-(4-anilinocarbonylphenoxymethyl)tetrahydropyran-2-yloxy]-2,4-dichlorophenethyl}imidazole
109. 1-{β-[6-(4-1'-piperazinylphenoxymethyl)tetrahydropyran-2-yloxy]-2,4-dichlorophenethyl}imidazole
110. 1-{β-[6-(4-4'-methyl-1'-piperazinylphenoxymethyl)tetrahydropyran-2-yloxy]-2,4-dichlorophenethyl}imidazole
111. 1-{β-[6-(4-4'-acetyl-1'-piperazinylphenoxymethyl)-tetrahydropyran-2-yloxy]-2,4-dichlorophenethyl}-imidazole
112. 1-{β-[6-(4-4'-acetyl-1'-piperazinyl-2,6-dichlorophenoxymethyl)tetrahydropyran-2-yloxy]-2,4-dichlorophenethyl}imidazole
113. 1-{β-[6-(4-4'-benzoyl-1'-piperazinylphenoxymethyl)tetrahydropyran-2-yloxy]-2,4-dichlorophenethyl}imidazole
114. 1-[β-(6-benzyloxymethyltetrahydropyran-2-yloxy)-2,4-dichlorophenethyl]imidazole
115. 1-{β-[6-(4-chlorobenzyloxymethyl)tetrahydropyran-2-yloxy]-2,4-dichlorophenethyl}imidazole
116. 1-{β-[6-(4-chlorobenzylthiomethyl)tetrahydropyran-2-yloxy]-2,4-dichlorophenethyl}imidazole
117. 1-{β-[6-(4-fluorobenzyloxymethyl)tetrahydropyran-2-yloxy]-2,4-dichlorophenethyl}imidazole
118. 1-{β-[6-(2,4-dichlorobenzyloxymethyl)tetrahydropyran-2-yloxy]-2,4-dichlorophenethyl}imidazole
119. 1-{β-[6-(2,6-dichlorobenzyloxymethyl)tetrahydropyran-2-yloxy]-2,4-dichlorophenethyl}imidazole
120. 1-{β-[6-(5-bromo-2-chlorobenzyloxymethyl)tetrahydropyran-2-yloxy]-2,4-dichlorophenethyl}-imidazole
121. 1-{β-[6-(2,4-dimethylbenzyloxymethyl)tetrahydropyran-2-yloxy]-2,4-dichlorophenethyl}imidazole
122. 1-{β-[6-(2,4-dimethoxybenzyloxymethyl)tetrahydropyran-2-yloxy]-2,4-dichlorophenethyl}imidazole
123. 1-{β-[6-(3,4,5-trimethoxybenzyloxymethyl)tetrahydropyran-2-yloxy]-2,4-dichlorophenethyl}-imidazole
124. 1-{β-[6-(4-4'-acetyl-1'-piperazinylbenzyloxymethyl)tetrahydropyran-2-yloxy]-2,4-dichlorophenethyl}imidazole
125. 1-{β-[6-(4-4'-acetyl-1'-piperazinyl-2-chlorobenzyloxymethyl)tetrahydropyran-2-yloxy]-2,4-dichlorophenethyl}imidazole
126. 1-{β-[6-(4-4'-benzyl-1'-piperazinyl-2-chlorobenzyloxymethyl)tetrahydropyran-2-yloxy]-2,4-dichlorophenethyl}imidazole 127. 1-[β-(6-α-naphthyloxymethyltetrahydropyran-2-yloxy)-2,4-dichlorophenethyl]imidazole
128. 1-[β-(6-α-naphthyloxymethyltetrahydropyran-2-yloxy)-2,4-dichlorophenethyl]-1H-1,2,4-triazole
129. 1-{β-[6-(2,4-dichlorophenoxymethyl)tetrahydropyran-2-yloxy]-4-methylphenethyl}-1H-1,2,4-triazole
130. 1-{β-[6-(2,4-dichlorophenoxymethyl)tetrahydropyran-2-yloxy]-4-methoxyphenethyl}imidazole
131. 1-{β-[6-(2,4-dichlorophenoxymethyl)tetrahydropyran-2-yloxy]-4-methoxyphenethyl}-1H-1,2,4-triazole
132. 1-{3-(4-fluorophenyl)-3-[6-(4-fluorophenoxymethyl)tetrahydropyran-2-yloxy]propyl}imidazole
133. 1-{3-[6-(2,4-dichlorophenoxymethyl)tetrahydropyran-2-yloxy]-3-(4-fluorophenyl)propyl}imidazole
134. 1-{3-[6-(2,4-dichlorophenoxymethyl)tetrahydropyran-2-yloxy]-3-(4-fluorophenyl)propyl}-1H-1,2,4-triazole
135. 1-{3-[6-(4-chloro-2-methylphenoxymethyl)tetrahydropyran-2-yloxy]-3-(4-fluorophenyl)propyl}-imidazole
136. 1-{3-[6-(4-acetamidophenoxymethyl)tetrahydroyran-2-yloxy]-3-(4-fluorophenyl)propyl}imidazole
137. 1-{3-[6-(4-chlorobenzylthiomethyl)tetrahydropyran-2-yloxy]-3-(4-fluorophenyl)propyl}imidazole
138. 1-{4-(4-chlorophenyl)-2-[6-(4-chlorophenylthiomethyl)tetrahydropyran-2-yloxy]butyl}imidazole
139. 1-{2-[6-(2,4-dichlorophenoxymethyl)tetrahydropyran-2-yloxy]-4-(4-chlorophenyl)butyl}imidazole
140. 1-{2-[6-(4-chloro-2-methylphenoxymethyl)tetrahydropyran-2-yloxy]-4-(4-chlorophenyl)butyl}-imidazole
141. 1-{2-[6-(4-acetamidophenoxymethyl)tetrahydropyran-2-yloxy]-4-(4-chlorophenyl)butyl}-1H-1,2,4-triazole
142. 1-{2-[6-(2,4-dichlorophenoxymethyl)tetrahydropyran-2-yloxy]-4-(2,4-dichlorophenyl)butyl}imidazole Of the above compounds, Compounds No. 8, 9, 38, 43, 45, 55, 63, 72, 87, 88, 95, 103, 111, 116, 125, 132 and 139 are especially preferred in view of their excellent activities, the trans-isomers of these compounds being most preferred.

Compounds of formula (IIa), as defined above, can be prepared by reacting a compound of formula (III):

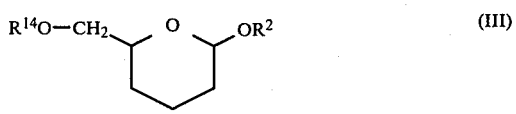

(in which $R^{14}$ represents a lower alkanesulphonyl group or an aranesulphonyl (arylsulphonyl)group and $R^2$ is as defined above) with a compound of formula (IV):

(wherein $R^{15}$ represents a hydrogen atom, an alkali metal atom or a group of formula —$CH_2$—$CH(R^3)$—OM, $R^3$ being as defined above and M representing an alkali metal atom, and Q is as defined above).

When $R^{15}$ in the compound of formula (IV) represents a hydrogen atom, the reaction between the compound of formula (III) and the compound of formula (IV) is preferably effected at a temperature of from 100° to 150° C., using an excess of the imidazole or 1,2,4-triazole of formula (IV).

If $R^{15}$ in the compound of formula (IV) represents an alkali metal atom or a group of formula —$CH_2$—$CH(R^3)$—OM, then the reaction is preferably effected at a temperature of from 50° C. to 100° C.

In either case, the reaction is preferably effected in the presence of a solvent, the nature of which is not critical, provided that it has no adverse effect upon the reaction. Suitable solvents include dimethyl sulphoxide, dimethylformamide and dimethylacetamide.

The resulting compound of formula (IIa) may then be separated from the reaction mixture by conventional means and, if desired, further purified by conventional means, for example chromatography.

The tetrahydrofuran starting material of formula (III) can be prepared as illustrated by the following reaction scheme:

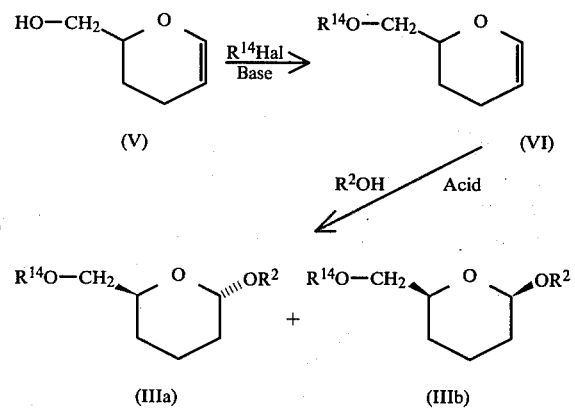

(in which $R^2$ and $R^{14}$ are as defined above and Hal represents a halogen atom, preferably a chlorine atom).

The reaction between the compound of formula (V) and the compound of formula $R^{14}Hal$ (e.g. methanesulphonyl chloride, benzenesulphonyl chloride or p-toluenesulphonyl chloride) is preferably carried out in the presence of an inert organic solvent (such as benzene, toluene, diethyl ether or tetrahydrofuran) and should be carried out in the presence of a base, such as pyridine or triethylamine. We particularly prefer to use pyridine as the base and to use it in a large excess, in which case it also functions as the solvent.

The reaction between the resulting compound of formula (VI) and the hydroxy compound of formula $R^2OH$ is also preferably carried out in the presence of a solvent, for example: an ether, such as diethyl ether, tetrahydrofuran, dimethyloxyethane or dioxan; or a halogenated hydrocarbon, such as methylene chloride or chloroform. This reaction is effected in the presence of an acid catalyst, for example: a mineral acid, such as hydrochloric acid or sulphuric acid; a phosphorus halide, such as phosphorus oxytrichloride or phosphorus pentachloride; a Lewis acid, such as boron trifluoride, tin tetrachloride or titanium tetrachloride; an organic acid, such as trifluoroacetic acid, dichloroacetic acid, monochloroacetic acid or p-toluenesulphonic acid; or an organic acid salt, such as pyridinium p-toluenesulphonate.

In this reaction, the trans-isomer (IIIa) and the cis-isomer (IIIb) are formed in a molar ratio which may range from 60:40 to 95:5. In general, it is desirable to separate the isomers in order to prepare the separate cis or trans isomer of the final product; this separation may be effected by conventional methods, such as recrystallization or column chromatography.

Compounds of formula (IIb), except for those in which a group of formula

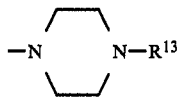

is present as a substituent on the phenyl or benzyl group represented by $R^{11}$, can be prepared by reacting a compound of formula (VII):

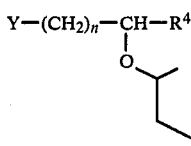

(VII)

(in which: n, $R^4$ and X are as defined above; Y represents a halogen atom, a lower alkanesulphonyloxy group or an aranesulphonyloxy (arylsulphonyloxy) group; and $R^{16}$ represents any one of the groups heretofore defined for $R^{11}$, except such groups having a substituent of formula

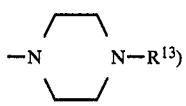

with a compound of formula (VIII):

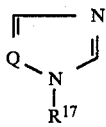

(VIII)

(in which Q is as defined above and $R^{17}$ represents a hydrogen atom or an alkali metal atom).

When $R^{17}$ in the compound of formula (VIII) represents a hydrogen atom, the compound of formula (VIII) is preferably employed in a molar excess and the reaction is preferably carried out at a temperature of from 100° C. to 150° C. On the other hand, when $R^{17}$ in the compound of formula (VIII) represents an alkali metal atom, the reaction is preferably carried out at a temperature of from 50° C. to 100° C. In either case, the reaction is preferably effected in the presence of an organic solvent, the nature of which is not critical, provided that it has no adverse effect upon the reaction. Suitable solvents include dimethyl sulphoxide, dimethylformamide and dimethylacetamide.

The tetrahydropyran starting material of formula (VII) can be prepared by the reaction summarized in the following reaction scheme:

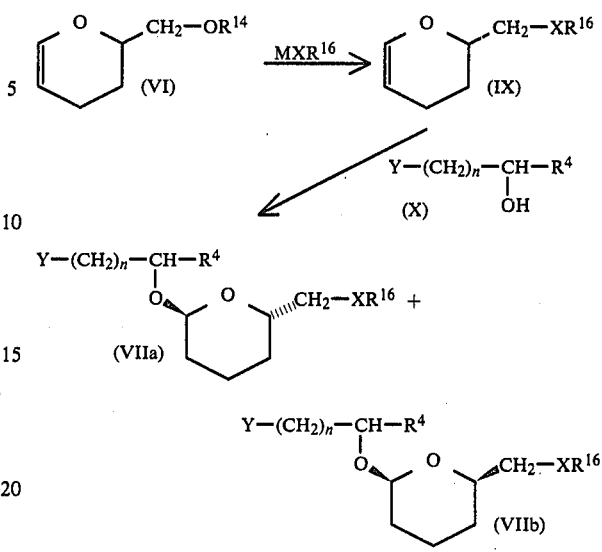

(in which $R^4$, $R^{14}$, $R^{16}$, X, Y and n are as defined above). $R^{14}$ preferably represents a methanesulphonyl, benzenesulphonyl or p-toluenesulphonyl group.

The compound of formula (VI), which is the starting material for the above reaction scheme, may be prepared as hereinbefore described in connection with the preparation of the starting materials for use in the production of compounds of formula (IIa). The reaction between the compound of formula (VI) and the compound of formula $MXR^{16}$ is preferably effected in the presence of an inert organic solvent (such as dimethyl sulphoxide, dimethylformamide, benzene or tetrahydrofuran) at a temperature of from 50° C. to 100° C.

The resulting compound of formula (IX) is then reacted with a hydroxy compound of formula (X), preferably in the presence of an acid catalyst, to give the desired starting material of formula (VII). The reaction is preferably effected in the presence of an inert organic solvent, for example: an ether, such as diethyl ether, tetrahydrofuran, dimethoxyethane or dioxan; or a halogenated hydrocarbon, such as methylene chloride or chloroform. Suitable acid catalysts include those hereinbefore exemplified for the conversion of a compound of formula (VI) to a compound of formula (III).

The resulting compound of formula (VII) exists in the form of a trans isomer (VIIa) and a cis isomer (VIIb). In this reaction, the trans and cis isomers are generally formed in a molar ratio of from 60:40 to 95:5. These isomers may, if desired, be separated by conventional means, for example recrystallization or column chromatography.

Compounds of formula (IIb) may also be prepared by the following sequence of reactions:

(a) reacting a compound of formula (XI):

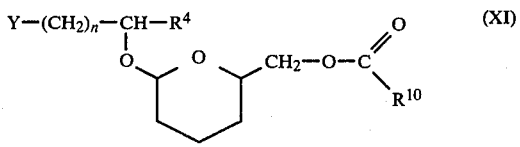

(in which Y, n, $R^4$ and $R^{10}$ are as defined above) with a compound of formula (VIII):

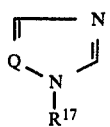 (VIII)

(in which Q and $R^{17}$ are as defined above) to give a compound of formula (XII):

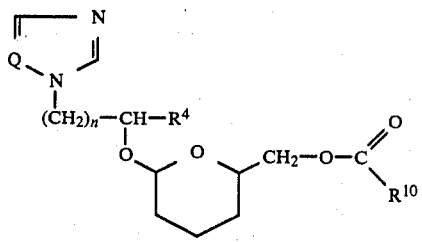 (XII)

(in which Q, n, $R^4$ and $R^{10}$ are as defined above);

(b) optionally hydrolyzing said compound of formula (XII) to give a compound of formula (XIII):

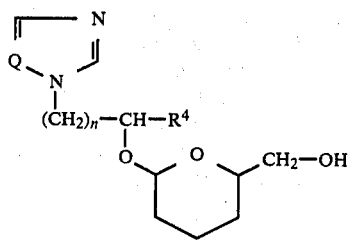 (XIII)

(in which Q, n and $R^4$ are as defined above);

(c) optionally sulphonylating said compound of formula (XIII) to give a compound of formula (XIV):

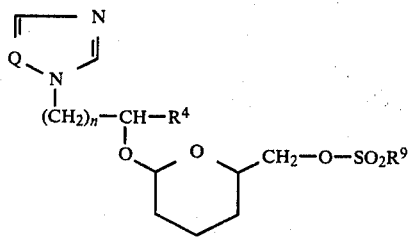 (XIV)

(in which Q, n, $R^4$ and $R^9$ are as defined above); and (d) optionally reacting said compound of formula (XIV) with a compound of formula $MXR^{18}$ (in which M and X are as defined above and $R^{18}$ represents any one of the groups hereinbefore defined for $R^{11}$, other than a hydrogen atom or the groups of formula $-CO.R^{10}$ and $SO_2R^9$ to give a compound of formula (XV):

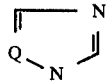 (XV)

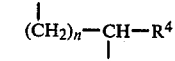

Each of the compounds of formulae (XII), (XIII) and (XIV), prepared in the course of the above sequence of reactions, as well as the final product of formula (XV), is a compound of the present invention, although said compounds of formulae (XII), (XIII) and (XIV) find their principal uses as intermediates in the preparation of the compounds of formula (XV) and other similar compounds.

Step (a) of the above reaction sequence, that is to say the reaction of said compound of formula (XI) with said compound of formula (VIII), is preferably effected under the same conditions as are used in the reaction between said compound of formula (VIII) and the compound of formula (VII) to prepare the compounds of formula (IIb).

The hydrolysis reaction of step (b) of the above reaction sequence is preferably effected as an alkaline hydrolysis. Suitable alkalies for use in this step include sodium hydroxide, potassium hydroxide, sodium carbonate and sodium bicarbonate. The reaction is preferably effected in aqueous solution or in a water-soluble organic solvent (such as methanol, ethanol or tetrahydrofuran). The temperature at which the reaction is effected is preferably from ambient temperature to the reflux temperature of the reaction mixture.

Step (c) of the above reaction sequence comprises the sulphonylation of the compound of formula (XIII) to give a compound of formula (XIV). This reaction is preferably effected by reacting the chosen sulphonyl halide (for example p-toluenesulphonyl chloride, benzenesulphonyl chloride or methanesulfonyl chloride) with said compound of formula (XIII). The reaction is preferably effected in an organic solvent (such as benzene, toluene, diethyl ether or tetrahydrofuran) and in the presence of a base (such as pyridine or triethylamine).

Finally, the reaction in step (d) between the compound of formula (XIV) and the compound of formula $MXR^{18}$ is preferably effected in the presence of an organic solvent (such as dimethyl sulphoxide, dimethylformamide, benzene or tetrahydrofuran) at a temperature of from 50° C. to 100° C.

The products of steps (a)-(d) may, if desired, be isolated from the reaction mixture by conventional means and, if desired, the products may be purified by conventional means such as recrystallization or chromatography. In the case of the products of step (a), (b) and (c), however, they may be used in subsequent steps in the reaction sequence without intermediate isolation or without purification.

The compound of formula (XI), which is a starting material in the above reaction sequence may be prepared by reacting a compound of formula (XVI):

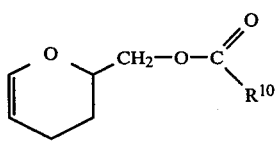

(XVI)

(in which $R^{10}$ is as defined above) with a compound of formula (X):

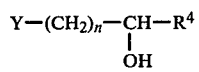

(X)

(in which Y, n and $R^4$ are as defined above). This reaction is preferably effected in the presence of an acid catalyst and under the conditions and using the materials suggested in relation to the preparation of the similar compounds of formula (VII).

The compounds of formula (I), as well as their acid addition salts and metal complexes, have been found to exhibit antifungal, antibacterial and antiprotozoal activities, including activity against such microorganisms which are pathogenic to human beings and other animals. Examples of fungi against which the compounds of the invention are active include: *Nocardi asteroides, Candida albicans, Candida tropicalis, Candida pseudotropicalis, Cryptococcus albidus, Cryptococcus neoformans, Rhodotorula glutinis, Torulopsis candida, Torulopsis colliculosa, Trichosporon cutaneum, Geotrichum candidum, Aspergillus fumigatus, Aspergillus candidus, Hormodendrum pedrosoi, Microsporum gypseum, Philaphora verrucosa, Sporothrix schenckii, Trichophyton interdigitale, Trichophyton ruburum, Trichophyton mentagrophytes,* as well as species of the genus Saprolegnia. The compounds are also active against bacteria, such as *Staphylococcus aureus,* and against protozoa, such as *Trichomonas vaginalis* and *Trichomonas foetus.* Although such activities mean that the compounds of the invention are, of course, of considerable value in pharmaceutical applications, they are not limited to use as pharmaceuticals. For example, they are useful as antibacterial or antimycotic agents in foods to protect the foods from deterioration and decay caused by bacteria and fungi.

For pharmaceutical applications, the pharmaceutical composition of the invention may be a solid, semi-solid or liquid, particularly in the form of a tablet, capsule, powder, suppository, suspension, emulsion, lotion or ointment. Suitable pharmaceutically acceptable (i.e. non-toxic) carriers and diluents conventionally employed are as follows: for solid preparations, tricalcium phosphate, calcium carbonate, kaolin, bentonite, talc, gelatin, lactose or starch; for semi-solid preparations, emulsion bases such as polyalkylene glycols or petrolatums; and for liquid preparations, water, vegetable oil and low boiling point solvents such as isopropanol or hydrogenated naphthalene.

The pharmaceutical composition containing at least one of the compounds of the present invention may also be blended with conventional pharmaceutical excipients, such as antiseptics, stabilizers, emulsions, salts to control osmotic pressure and buffering agents. It is also possible to incorporate into the composition compounds having other therapeutic activities.

For pharmaceutical applications, the compounds and compositions of the present invention can be administered to humans and other animals by conventional methods, such as topical, parenteral (particularly intramuscular, subcutaneous or intravenous) or oral administration. For topical applications, the zones in which the fungi, bacteria or protozoa to be eradicated proliferate or the zones which should be protected from invasion of such fungi, bacteria or protozoa may be treated with the compounds or compositions of the invention by such means as dusting, spraying, atomizing, rinse brushing, immersion, coating, covering or impregnation. Pharmaceutical compositions for topical application may contain the compounds of the invention in a wide range of concentrations, for example from 0.1 to 10% by weight.

In general, for systemic administration (e.g. oral or parenteral administration), the delay dosage is preferably from 1 to 100 mg/kg body weight and more preferably from 5 to 50 mg/kg, this preferably being administered in divided doses. In the case of topical administration, the amount employed will generally be less than this, although the precise amount will vary depending upon the condition to be treated or prevented.

The preparation of the compounds of the invention is further illustrated by the following Examples.

EXAMPLE 1

1-[6-(4-chlorobenzyloxy)tetrahydropyran-2-ylmethyl]imidazole (a) Cis- and trans-6-(4-chlorobenzyloxy)-2-tosyloxymethyltetrahydropyran 3 g of 2-tosyloxymethyl-3,4-dihydro-2H-pyran and 1.91 g of p-chlorobenzyl alcohol were dissolved in 40 ml of diethyl ether, and 2–3 drops of phosphorus oxytrichloride were added to the resulting solution. The mixture was then allowed to react at room temperature for 1.5 days, after which 2 drops of triethylamine were added and the mixture was concentrated by evaporation under reduced pressure. The residue was subjected to column chromatography through silica gel, eluted with a 8:1 by volume mixture of hexane and ethyl acetate, to give 3.44 g of trans-6-(4-chlorobenzyloxy)-2-tosyloxymethyltetrahydropyran (having the lesser polarity), 0.59 g of cis-6-(4-chlorobenzyloxy)-2-tosyloxymethyltetrahydropyran (having the greater polarity) and 0.86 g of an approximately 1:1 cis/trans mixture.

Trans-isomer:

Infrared Absorption Spectrum (liquid film)$\nu_{max}$cm$^{-1}$: 1600, 1500, 1360, 1180.

Nuclear Magnetic Resonance Spectrum (CDCl$_3$, 60 MHz) δ ppm: 1.3–2.0 (6H, multiplet); 2.40 (3H, singlet); 3.8–4.2 (1H, multiplet); 4.40 (1H, AB-doublet, J=12 Hz); 4.65 (1H, AB-doublet, J=12 Hz); 4.85 (1H, broad singlet); 7.3–7.5 (6H, multiplet); 7.85 (2H, doublet, J=9 Hz).

Cis-isomer:

Infrared Absorption Spectrum (liquid film) $\nu_{max}$cm$^{-1}$: 1600, 1490, 1360, 1180.

Nuclear Magnetic Resonance Spectrum (CDCl$_3$, 60 MHz) δ ppm: 1.0–2.0 (6H, multiplet); 2.40 (3H, singlet); 3.40–4.0 (1H, multiplet); 4.02 (1H, singlet); 4.06 (1H, doublet, J=5 Hz); 4.3–4.7 (1H, multiplet); 4.50 (1H, AB-doublet, J=12 Hz); 4.75 (1H, AB-doublet, J=12 Hz); 7.2–7.5 (6H, multiplet); 7.85 (2H, doublet, J=8 Hz).

(b) Trans-1-[6-(4-chlorobenzyloxy)tetrahydropyran-2-ylmethyl]imidazole

A mixture of 0.28 g (12 mmoles) of 50% sodium hydride (i.e. 50% w/w sodium hydride in mineral oil) and 0.817 g (12 mmoles) of imidazole was stirred in 25 ml of dimethylformamide at 80° C. for 30 minutes. The mixture was then left to cool at room temperature, after which there was added a solution of 3.30 g of trans-6-(4-chlorobenzyloxy)-2-tosyloxymethyltetrahydropyran in 5 ml of dimethylformamide, at room temperature, and then the mixture was heated at 80°–85° C. for 2 hours. After cooling the mixture, it was poured into ice-water and then extracted with diethyl ether. The ethereal extract was washed with an aqueous solution of sodium chloride and dried over anhydrous sodium sulphate, after which the solvent was evaporated off. The residue was purified by column chromatography through 50 g of silica gel eluted with a 30:1:1 by volume mixture of ethyl acetate, ethanol and triethylamine, to give 2.21 g of the title compound as a colourless oil.

Infrared Absorption Spectrum (liquid film) $\nu_{max}$cm$^{-1}$: 1600, 1495, 1120, 1030.

Nuclear Magnetic Resonance Spectrum (CDCl$_3$, 60 MHz) δ ppm: 1.0–2.0 (6H, multiplet); 3.93 (2H, doublet, J=2 Hz); 3.6–4.2 (1H, multiplet); 4.3 (2H, AB-doublet, J=13 Hz); 4.92 (1H, broad singlet); 6.95–7.7 (7H, multiplet).

(c) Cis-1-[6-(4-chlorobenzyloxy)tetrahydropyran-2-ylmethyl]imidazole

The sodium salt of imidazole was prepared from 48 mg of sodium hydride and 0.14 g of imidazole, as described in Example 1(b), and then, as in Example 1(b), a dimethylformamide solution of 0.55 g of cis-6-(4-chlorobenzyloxy)-2-tosyloxymethyltetrahydropyran was added and the mixture was reacted, after which the product was separated and purified as in Example 1(b), to give 342 mg of the title compound in the form of an oil.

Infrared Absorption Spectrum (liquid film) $\nu_{max}$cm$^{-1}$: 1595, 1495, 1140, 1060.

Nuclear Magnetic Resonance Spectrum (CDCl$_3$, 60 MHz) δ ppm: 1.0–2.0 (6H, multiplet); 3.3–4.0 (1H, multiplet); 4.0 (1H, singlet); 4.05 (2H, doublet, J=5 Hz); 4.2–4.5 (1H, multiplet); 4.5 (1H, AB-doublet, J=12 Hz); 4.75 (1H, AB-doublet, J=12 Hz); 6.95–7.7 (7H, multiplet).

EXAMPLE 2

1-[6-(2,4-dichlorobenzyloxy)tetrahydropyran-2-ylmethyl]imidazole (a) Cis- and trans-6-(2,4-dichlorobenzyloxy)-2-tosyloxymethyltetrahydropyran To a solution of 1.34 g of 2-tosyloxymethyl-3,4-dihydro-2$\underline{H}$-pyran in 25 ml of diethyl ether were added 1.06 g of 2,4-dichlorobenzyl alcohol, followed by a catalytic amount (2–3 drops) of phosphorus oxytrichloride. The mixture was then stirred at room temperature for 4 days, after which 3 drops of triethylamine were added to the mixture, which was then concentrated by evaporation under reduced pressure. The residue was purified by column chromatography through silica gel as in Example 1(a), to give 1.82 g of trans-6-(2,4-dichlorobenzyloxy)-2-tosyloxymethyltetrahydropyran (having the lesser polarity), 144 mg of cis-6-(2,4-dichlorobenzyloxy)-2-tosyloxymethyltetrahydropyran (having the greater polarity) and 200 mg of a cis/trans mixture.

Trans-isomer:
Infrared Absorption Spectrum (liquid film) $\nu_{max}$cm$^{-1}$: 1595, 1560, 1470, 1450, 1360, 1190.

Nuclear Magnetic Resonance Spectrum (CDCl$_3$, 60 MHz) δ ppm: 1.0–2.0 (6H, multiplet); 2.40 (3H, singlet); 3.97 (2H, doublet, J=2 Hz); 3.8–4.2 (1H, multiplet); 4.42 (1H, AB-doublet, J=13 Hz); 4.66 (1H, AB-doublet, J=13 Hz); 4.87 (1H, broad singlet); 7.1–7.6 (5H, multiplet); 7.80 (2H, doublet, J=8 Hz).

Cis-isomer:
Infrared Absorption Spectrum (liquid film) $\nu_{max}$cm$^{-1}$: 1600, 1480, 1370, 1180.

Nuclear Magnetic Resonance Spectrum (CDCl$_3$, 60 MHz) δ ppm: 1.0–2.2 (6H, multiplet); 2.40 (3H, singlet); 3.4–3.95 (1H, multiplet); 4.03 (1H, doublet, J=4 Hz); 4.06 (1H, doublet, J=5 Hz); 4.35–4.70 (1H, multiplet); 4.73 (2H, AB-doublet, J=15 Hz); 7.0–7.6 (5H, multiplet); 7.80 (2H, doublet, J=8 Hz).

(b) Trans-1-[6-(2,4-dichlorobenzyloxy)tetrahydropyran-2-ylmethyl]imidazole

As in Example 1(b), 5 ml of a dimethylformamide solution containing 1.70 g of trans-6-(2,4-dichlorobenzyloxy)-2-tosyloxymethyltetrahydropyran were added to 15 ml of a dimethylformamide solution containing 5.73 mmoles of the sodium salt of imidazole and the mixture was allowed to react for 2 hours at 85° C., after which it was treated and purified as in Example 1(b), to give 1.2 g of the title compound as a colourless oil.

Infrared Absorption Spectrum (liquid film) $\nu_{max}$cm$^{-1}$: 1590, 1500, 1470.

Nuclear Magnetic Resonance Spectrum (CDCl$_3$, 60 MHz) δ ppm: 1.2–2.0 (6H, multiplet); 3.86 (2H, broad singlet); 3.7–4.15 (1H, multiplet); 4.1–4.7 (2H, multiplet); 4.90 (1H, broad singlet); 6.9–7.6 (6H, multiplet).

(c) Nitric acid salt of trans-isomer

A solution of 806 mg of trans-1-[6-(2,4-dichlorobenzyloxy)tetrahydropyran-2-ylmethyl]imidazole in 10 ml of diethyl ether was cooled on an ice-water bath, and then 0.18 ml of 69% w/v aqueous nitric acid was added thereto, with cooling, upon which an oily product separated. After decanting off the ethereal layer, the precipitate was washed with diethyl ether and then crystallized. The crystals formed were filtered, dried and then recrystallized from benzene to give the title compound, melting at 84°–85° C.

(d) Hydrochloric acid salt of trans-isomer

Whilst cooling a solution of 270 mg of trans-1-[6-(2,4-dichlorobenzyloxy)tetrahydropyran-2-ylmethyl]imidazole on an ice-water bath, 2.5 ml of a saturated ethereal solution of hydrogen chloride were added thereto, giving 231 mg of the title compound, melting at 80°–84° C.

(e) Oxalic acid salt of trans-isomer

To a solution of 440 mg of trans-1-[6-(2,4-dichlorobenzyloxy)tetrahydropyran-2-ylmethyl]imidazole in 4 ml of diethyl ether, which was being cooled on an ice-water bath, were added 1.5 ml of an ethereal solution containing 139 mg of oxalic acid, after which the solution was crystallized and filtered as in (c) above and then the product was recrystallized from a mixture of methanol and ethanol, to give 500 mg of the title compound, melting at 134°–136° C.

(f) Cis-1-[6-(2,4-dichlorobenzyloxy)tetrahydropyran-2-ylmethyl]imidazole

As in Example 1(b), 16 mg of imidazole, 10 mg of 55% sodium hydride and 70 mg of cis-6-(2,4-dichlorobenzyloxy)-2-tosyloxymethyltetrahydropyran were reacted in dimethylformamide, to give 37 mg of the title compound in the form of a colourless oil.

Infrared Absorption Spectrum (liquid film) $\nu_{max}$cm$^{-1}$: 1590, 1480, 1080, 1040.

Nuclear Magnetic Resonance Spectrum (CDCl$_3$, 60 MHz) δ ppm: 1.2–2.3 (6H, multiplet); 3.5–4.0 (1H, multiplet); 4.03 (2H, doublet, J=6 Hz); 4.3–4.7 (1H, multiplet); 4.73 (2H, AB-doublet, J=12 Hz); 6.9-7.7 (6H, multiplet).

EXAMPLE 3

(a) Trans-1-[6-(2,4-dichlorobenzyloxy)tetrahydropyran-2-ylmethyl]-1H-1,2,4-triazole Following the procedure described in Example 1(b), the sodium salt of 1,2,4-triazole was prepared from 188 mg of 55% sodium hydride and 298 mg of 1,2,4-triazole in dimethylformamide, and then 10 ml of a dimethylformamide solution containing 1.28 g of trans-6-(2,4-dichlorobenzyloxy)-2-tosyloxymethyltetrahydropyran were added thereto. The mixture was allowed to react at 85° C. for 2 hours, after which the product was treated and purified essentially as described in Example 1(b), to give 866 mg of the title compound in the form of a colourless oil.

Infrared Absorption Spectrum (liquid film) $\nu_{max}$cm$^{-1}$: 1580, 1500, 1270, 1200, 1010.

Nuclear Magnetic Resonance Spectrum (CDCl$_3$, 60 MHz) δ ppm: 1.2-2.1 (6H, multiplet); 3.9-4.4 (5H, multiplet); 4.87 (1H, broad singlet); 7.0-7.4 (3H, multiplet); 7.80 (1H, singlet); 8.03 (1H, singlet).

(b) Hemi[zinc(II)chloride] complex of product of step (a)

To 0.5 ml of a methanolic solution containing 230 mg of trans-1-[6-(2,4-dichlorobenzyloxy)tetrahydropyran-2-ylmethyl]-1H-1,2,4-triazole were added 0.5 ml of a methanolic solution containing 183 mg of zinc chloride. After allowing the mixture to react at room temperature for 30 minutes, it was poured into 15 ml of cold water and the crystals which precipitated were filtered off, giving the title compound in the form of a crystalline solid melting at 57°-59° C.

EXAMPLE 4

1-[6-(2,6-Dichlorobenzyloxy)tetrahydropyran-2-ylmethyl]imidazole (a) Cis- and trans-6-(2,6-dichlorobenzyloxy)-2-tosyloxymethyltetrahydropyran To a solution of 1.34 g of 2-tosyloxymethyl-3,4-dihydro-2H-pyran and 1.06 g of 2,6-dichlorobenzyl alcohol in 25 ml of diethyl ether was added a catalytic amount (2 drops) of phosphorus oxytrichloride, and then the mixture was stirred at room temperature for 4 days. The colourless crystals which had precipitated were filtered off, giving 1.582 g of trans-6-(2,6-dichlorobenzyloxy)-2-tosyloxymethyltetrahydropyran, melting at 123°-124° C. Triethylamine was then added to the mother liquor and the resulting mixture was evaporated under reduced pressure and the residue purified by column chromatography through silica gel, in essentially the same manner as described in Example 1(a), to give 338 mg of trans-6-(2,6-dichlorobenzyloxy)-2-tosyloxymethyltetrahydropyran and 306 mg of cis-6-(2,6-dichlorobenzyloxy)-2-tosyloxymethyltetrahydropyran.

Trans-isomer:

Infrared Absorption Spectrum (Nujol-trademark) $\nu_{max}$cm$^{-1}$: 1600, 1590, 1565, 1460, 1435.

Nuclear Magnetic Resonance Spectrum (CDCl$_3$, 60 MHz) δ ppm: 1.30-1.95 (6H, multiplet); 2.42 (3H, singlet); 3.96 (2H, singlet); 4.00 (1H, multiplet); 4.54 (1H, AB-doublet, J=12 Hz); 4.91 (1H, AB-doublet, J=12 Hz); 4.94 (1H, broad singlet); 7.32 (5H, multiplet); 7.83 (2H, doublet, J=8 Hz).

Cis-isomer:

Infrared Absorption Spectrum (liquid film) $\nu_{max}$cm$^{-1}$: 1595, 1580, 1560, 1455, 1435.

Nuclear Magnetic Resonance Spectrum (CDCl$_3$, 60 MHz) δ ppm: 1.10-2.0 (6H, multiplet); 2.43 (3H, singlet); 3.73 (1H, miltiplet); 4.00 (1H, singlet); 4.07 (1H, doublet, J=5 Hz); 4.50 (1H, multiplet); 7.31 (5H, multiplet); 7.85 (2H, doublet, J=8 Hz).

(b) Trans-1-[6-(2,6-dichlorobenzyloxy)tetrahydropyran-2-ylmethyl]imidazole 196 mg of 55% sodium hydride were added to a solution of 306 mg of imidazole in 14 ml of dimethylformamide and the mixture was stirred at 80° C. for 30 minutes. The mixture was then cooled to room temperature, after which 1.335 g of trans-6-(2,6-dichlorobenzyloxy)-2-tosyloxymethyltetrahydropyran and 450 mg of sodium iodide were added thereto; the mixture was then stirred at 80°-85° C. for 2 hours. At the end of this time, the mixture was treated and purified essentially as described in Example 1(b), to give 965 mg of the title compound in the form of a colourless oil.

Infrared Absorption Spectrum (liquid film) $\nu_{max}$cm$^{-1}$: 1585, 1565, 1505.

Nuclear Magnetic Resonance Spectrum (CDCl$_3$, 60 MHz) δ ppm: 1.16-2.03 (6H, multiplet); 3.80-4.32 (3H, multiplet); 4.60 (1H, AB-doublet, J=12 Hz); 4.85 (1H, AB-doublet, J=12 Hz); 5.08 (1H, broad singlet); 7.03-7.76 (6H, multiplet).

(c) Nitric acid salt of trans-isomer

When 0.2 ml of 69% w/v aqueous nitric acid was added to a solution of 865 mg of trans-1-[6-(2,6-dichlorobenzyloxy)tetrahydropyran-2-ylmethyl]imidazole in 10 ml of diethyl ether, the solution became turbid and an oily layer separated. After decanting off the ethereal layer, more diethyl ether was added to the residue to aid crystallization and the precipitated crystals were filtered, to give 846 g of the title product. Further recrystallization of these crystals from a mixture of acetone and ethyl acetate gave the title product in the form of colourless crystals melting at 117° C.

(d) Cis-1-[6-(2,6-dichlorobenzyloxy)tetrahydropyran-2-ylmethyl]imidazole

Using 103 mg of imidazole, 66 mg of 55% sodium hydride and 161 mg of cis-6-(2,6-dichlorobenzyloxy)-2-tosyloxymethyltetrahydropyran, the procedure described in Example 1(b) was repeated to give 132 mg of the title product in the form of a colourless oil.

Infrared Absorption Spectrum (liquid film) $\nu_{max}$cm$^{-1}$: 1585, 1560, 1505.

Nuclear Magnetic Resonance Spectrum (CDCl$_3$, 60 MHz) δ ppm: 0.80-2.15 (6H, multiplet); 3.40-4.18 (3H, multiplet); 4.50 (1H, multiplet); 4.78 (1H, AB-doublet, J=12 Hz); 5.15 (1H, AB-doublet, J=12 Hz); 6.92-7.70 (6H, multiplet).

EXAMPLES 5-9

The following compounds were synthesized essentially as described in Examples 1-4.

EXAMPLE 5

Trans-1-(6-benzyloxytetrahydropyran-2-ylmethyl)imidazole

Infrared Absorption Spectrum (liquid film) $\nu_{max}$cm$^{-1}$: 1500, 1450, 1400.

Nuclear Magnetic Resonance Spectrum (CDCl$_3$, 60 MHz) δ ppm: 1.1-2.0 (6H, multiplet); 3.93 (3H, multiplet); 4.38 (2H, AB-doublet, J=12 Hz); 4.94 (1H, singlet); 7.01 (1H, singlet); 7.11 (1H, singlet); 7.34 (5H, multiplet); 7.58 (1H, singlet).

Cis-1-(6-benzyloxytetrahydropyran-2-ylmethyl)imidazole

Infrared Absorption Spectrum (liquid film) $\nu_{max}$cm$^{-1}$: 1502, 1457, 1440.

Nuclear Magnetic Resonance Spectrum (CDCl$_3$, 60 MHz) δ ppm:

1.0-2.0 (6H, multiplet); 3.55 (1H, multiplet); 3.92 (1H, singlet); 4.01 (1H, broad singlet); 4.38 (1H, multiplet); 4.67 (2H, AB-quartet, J=12 Hz); 7.02 (1H, broad singlet); 7.10 (1H, singlet); 7.34 (5H, multiplet); 7.58 (1H, singlet).

EXAMPLE 6

Trans-1-[6-(2-phenoxybenzyloxy)tetrahydropyran-2-ylmethyl]imidazole

Infrared Absorption Spectrum (liquid film) $\nu_{max}$cm$^{-1}$: 1580, 1480, 1230.

Nuclear Magnetic Resonance Spectrum (CDCl$_3$, 60 MHz) δ ppm: 1.0-1.9 (6H, multiplet); 3.6-4.2 (1H, multiplet); 3.88 (2H, singlet); 4.4 (1H, AB-doublet, J=12 Hz); 4.6 (1H, AB-doublet, J=12 Hz); 4.95 (1H, broad singlet); 6.8-7.6 (12H, multiplet).

Cis-1-[6-(2-phenoxybenzyloxy)tetrahydropyran-2-ylmethyl]imidazole

Infrared Absorption Spectrum (liquid film) $\nu_{max}$cm$^{-1}$: 1590, 1490, 1240.

Nuclear Magnetic Resonance Spectrum (CDCl$_3$, 60 MHz) δ ppm: 1.0-2.0 (6H, multiplet); 3.3-3.8 (1H, multiplet); 3.86 (1H, singlet); 3.88 (1H, doublet, J=5 Hz); 4.2-4.6 (1H, multiplet); 4.66 (1H, AB-doublet, J=13 Hz); 4.85 (1H, AB-doublet, J=13 Hz); 6.7-7.6 (12H, multiplet).

EXAMPLE 7

Trans-1-(6-t-butoxytetrahydropyran-2-ylmethyl)imidazole

Infrared Absorption Spectrum (liquid film) $\nu_{max}$cm$^{-1}$: 1500, 1000.

Nuclear Magnetic Resonance Spectrum (CDCl$_3$, 60 MHz) δ ppm. 0.95 (9H, singlet); 1.10-1.8 (6H, multiplet); 3.6-3.9 (2H, multiplet); 3.9-4.3 (1H, multiplet); 5.04 (1H, broad singlet); 6.92 (2H, doublet, J=4 Hz); 7.4 (1H, singlet).

Cis-1-(6-t-butoxytetrahydropyran-2-ylmethyl)imidazole

Infrared Absorption Spectrum (liquid film) $\nu_{max}$cm$^{-1}$: 1500.

Nuclear Magnetic Resonance Spectrum (CDCl$_3$, 60 MHz) δ ppm: 1.00 (3H, singlet); 1.08 (6H, singlet); 1.2-2.0 (6H, multiplet); 3.3-3.8 (1H, multiplet); 3.8-4.1 (2H, multiplet); 4.3-4.65 (1H, multiplet); 7.0 (2H, broad singlet); 7.52 (1H, broad singlet).

EXAMPLE 8

Trans-1-(6-propargyloxytetrahydropyran-2-ylmethyl)imidazole

Infrared Absorption Spectrum (liquid film) $\nu_{max}$cm$^{-1}$: 3290, 2120, 1510.

Nuclear Magnetic Resonance Spectrum (CDCl$_3$, 60 MHz) δ ppm: 0.93-1.88 (6H, multiplet); 2.36 (1H, triplet, J=2.5 Hz); 3.93 (5H, multiplet); 4.96 (1H, singlet); 6.93 (1H, singlet); 7.00 (1H, singlet); 7.46 (1H, singlet).

Cis-1-(6-propargyloxytetrahydropyran-2-ylmethyl)imidazole

Infrared Absorption Spectrum (liquid film) $\nu_{max}$cm$^{-1}$: 3270, 2100, 1500.

Nuclear Magnetic Resonance Spectrum (CDCl$_3$, 60 MHz) δ ppm: 0.9-2.1 (6H, multiplet); 2.48 (1H, triplet, J=2.5 Hz); 3.73 (1H, multiplet); 4.00 (1H, singlet); 4.03 (1H, doublet, J=6 Hz); 4.28 (2H, doublet, J=2.5 Hz); 4.59 (1H, multiplet); 7.03 (2H, singlet); 7.53 (1H, singlet).

EXAMPLE 9

Trans-1-(6-phenoxytetrahydropyran-2-ylmethyl)imidazole

Melting point 96° C.

Nuclear Magnetic Resonance Spectrum (CDCl$_3$, 60 MHz) δ ppm: 0.92-2.27 (6H, multiplet); 3.54-4.22 (3H, multiplet); 5.50 (1H, singlet); 6.64-7.00 (8H, multiplet).

Cis-1-(6-phenoxytetrahydropyran-2-ylmethyl)imidazole

Infrared Absorption Spectrum (liquid film) $\nu_{max}$cm$^{-1}$: 1595, 1585, 1505, 1480, 1460.

Nuclear Magnetic Resonance Spectrum (CDCl$_3$, 60 MHz) δ ppm: 0.90-2.10 (6H, multiplet); 3.38-4.10 (3H, multiplet); 5.02 (1H, multiplet); 6.70-7.52 (8H, multiplet).

EXAMPLE 10

Trans-1-{6-[α-(4-chlorophenyl)-2,4-dichlorobenzyloxy]tetrahydropyran-2-ylmethyl}imidazole (a) Trans-6-[α-(4-chlorophenyl)-2,4-dichlorobenzyloxy]-2-tosyloxymethyltetrahydropyran 2.10 g of α-(4-chlorophenyl)-2,4-dichlorobenzyl alcohol and 1.78 of 2-tosyloxymethyl-3,4-dihydro-2H-pyran were dissolved in 40 ml of diethyl ester, and a catalytic amount (2 drops) of phosphorus oxytrichloride was added to the solution. The mixture was then stirred at room temperature for 4 days, after which 3 drops of triethylamine were added. The mixture was then concentrated by evaporation under reduced pressure and the residue was purified by column chromatography through silica gel eluted with a 15:5:1 by volume mixture of hexane, benzene and ethyl acetate, to give 3.41 g of the title compound in the form of a colourless oil.

(b) Trans-1-{6-[α-(4-chlorophenyl)-2,4-dichlorobenzyloxy]tetrahydropyran-2-ylmethyl}imidazole 114 mg of 55% sodium hydride were added to a solution of 323 mg of imidazole in 10 ml of dimethylformamide, and, after the mixture had been stirred at 80° C. for 30 minutes, it was cooled to room temperature. There were then added 2.20 g of trans-6-[α-(4-chlorophenyl)-2,4-dichlorobenzyloxy]-2-tosyloxymethyltetrahydropyran, dissolved in 15 ml of dimethylformamide, and then 594 mg of sodium iodide were added to the mixture. The resulting mixture stirred under a stream of nitrogen at 90°-95° C. for 4 hours, after which it was cooled, diluted with water and extracted with diethyl ether. The ethereal extract was washed with water and dried over sodium sulphate, after which it was concentrated by evaporation under reduced pressure and the residue was purified by column chromatography through silica gel eluted with a 8:1:0.1 by volume mixture of ethyl acetate, benzene and triethylamine, to give 1.346 g of the title compound as a colourless oil.

Infrared Absorption Spectrum (liquid film) $\nu_{max}$cm$^{-1}$: 1580, 1500, 1120, 1010.

Nuclear Magnetic Resonance Spectrum (CDCl$_3$, 60 MHz) δ ppm: 0.9–2.2 (6H, multiplet); 3.55–4.10 (3H, multiplet); 4.83 (1H, broad singlet); 5.77 and 5.87 (together 1H, singlet); 6.75–7.70 (11H, multiplet).

(c) Oxalic acid salt

To a solution of 1.60 g of trans-1-{6-[α-(4-chlorophenyl)-2,4-dichlorobenzyloxy]tetrahydropyran-2-ylmethyl}imidazole in 10 ml of diethyl ether were added 5 ml of an ethereal solution containing 383 mg of oxalic acid. A white oily product formed and this was separated and then washed several times with diethyl ether until it crystallized. The crystals were separated by filtration and then recrystallized from a mixture of methanol and diisopropyl ether, to give the title product in the form of colourless crystals melting at 83°–85° C.

EXAMPLES 11–13

The following compounds were synthesized following essentially the same procedure as described in Example 10.

EXAMPLE 11

Trans-1-[6-(α-methyl-2,4-dichlorobenzyloxy)tetrahydro pyran-2-ylmethyl]imidazole Isomer of Lesser Polarity Infrared Absorption Spectrum (liquid film) $\nu_{max}$cm$^{-1}$: 3100, 1585, 1560, 1505, 1490, 1460.

Nuclear Magnetic Resonance Spectrum (CDCl$_3$, 60 MHz) δ ppm: 1.27 (3H, doublet, J=7 Hz); 1.0–2.0 (6H, multiplet); 3.98 (2H, singlet); 3.84–4.32 (1H, multiplet); 4.62 (1H, broad singlet); 4.93 (1H, quartet, J=7 Hz); 6.97–7.63 (6H, multiplet).

Isomer of Greater Polarity

Infrared Absorption Spectrum (liquid film) $\nu_{max}$cm$^{-1}$: 3100, 1590, 1560, 1505, 1470, 1440.

Nuclear Magnetic Resonance Spectrum (CDCl$_3$, 60 MHz) δ ppm: 1.35 (3H, doublet, J=7 Hz); 1.0–2.0 (6H, multiplet); 3.66 (2H, singlet); 3.40–3.80 (1H, multiplet); 4.93 (1H, quartet, J=7 Hz); 5.06 (1H, broad singlet); 6.70 (1H, singlet); 6.98 (1H, singlet); 7.13–7.63 (4H, multiplet).

EXAMPLE 12

Trans-1-{6-[α-(4-fluorophenyl)-2,4-dichlorobenzyloxy]-tetrahydropyran-2-ylmethyl}imidazole Infrared Absorption Spectrum (liquid film) $\nu_{max}$cm$^{-1}$: 1610, 1590, 1510, 1230.

Nuclear Magnetic Resonance Spectrum (CDCl$_3$, 60 MHz) δ ppm: 0.9–2.0 (6H, multiplet); 3.8 (3H, broad singlet); 4.77 (1H, broad singlet); 5.67 (0.5H, singlet); 5.77 (0.5H, singlet); 6.7–7.8 (10H, multiplet).

EXAMPLE 13

Trans-1-{6-[α-(2-nitrophenyl)-4-chlorobenzyloxy]tetrahydropyran-2-ylmethyl}imidazole Infrared Absorption Spectrum (liquid film) $\nu_{max}$cm$^{-1}$: 1610, 1595, 1580, 1530, 1500, 1490.

Nuclear Magnetic Resonance Spectrum (CDCl$_3$, 60 MHz) δ ppm: 0.95–2.05 (6H, multiplet); 3.40–4.10 (1H, multiplet); 3.75 (2H, broad singlet); 4.80 (1H, singlet); 6.15 (1H, singlet); 6.75–7.92 (11H, multiplet).

EXAMPLE 14

Trans-1-{6-[α-(2,4-dichlorobenzyl)4-fluorobenzyloxy]-tetrahydropyran-2-ylmethyl}imidazole Trans-6-[α-(2,4-dichlorobenzyl)-4-fluorobenzyloxy]-2-tosyloxymethyltetrahydropyran Following the same procedure as described in Example 10(a), 546 mg of the title compound, in the form of a colourless oil, were prepared from 610 mg of α-(2,4-dichlorobenzyl)-4-fluorobenzyl alcohol (itself prepared from 2,4-dichlorobenzylmagnesium chloride and p-fluorobenzaldehyde) and 552 mg of 2-tosyloxymethyl-3,4-dihydro-2H-pyran.

Infrared Absorption Spectrum (liquid film) $\nu_{max}$cm$^{-1}$: 1600, 1500, 1360, 1190, 1180.

Nuclear Magnetic Resonance Spectrum (CDCl$_3$, 60 MHz) δ ppm: 0.8–2.0 (6H, multiplet); 2.40 (3H, singlet); 3.07 (2H, doublet, J=6 Hz); 3.4–4.2 (3H, multiplet); 4.4–5.2 (2H, multiplet); 6.7–8.0 (10H, multiplet).

(b) Trans-1-{6-[α-(2,4-dichlorobenzyl)-4-fluorobenzyloxy]tetrahydropyran-2-ylmethyl}imidazole Following essentially the same procedure as described in Example 10(b), the sodium salt of imidazole was prepared from 79 mg of imidazole and 51 mg of 55% sodium hydride in dimethylformamide, and then 540 mg of trans-6-[α-(2,4-dichlorobenzyl)-4-fluorobenzyloxy]-2-tosyloxymethyltetrahydropyran and 293 mg of sodium iodide were added thereto. After stirring the mixture at 90°–95° C. for 4 hours, it was treated and the product purified essentially as in Example 10(b), to give 207 mg of the title compound in the form of a colourless oil.

Infrared Absorption Spectrum (liquid film) $\nu_{max}$cm$^{-1}$: 1600, 1500, 1220.

Nuclear Magnetic Resonance Spectrum (CDCl$_3$, 60 MHz) δ ppm: 0.8–1.7 (6H, multiplet); 2.6–3.0 (2H, multiplet); 3.2–3.8 (1H, multiplet); 3.50 (2H, multiplet); 4.1–4.8 (2H, multiplet); 6.4–7.4 (10H, multiplet).

EXAMPLE 15

Trans-1-{6-[α-(2,4-dichlorobenzyl)benzyloxy]tetrahydropyran-2-ylmethyl}imidazole (a) Trans-6-[α-(2,4-dichlorobenzyl)benzyloxy]-2 tosyloxymethyltetrahydropyran Following essentially the same procedure as described in Example 10(a), 193 mg of the title compound were prepared from 105 mg of α-(2,4-dichlorobenzyl)-benzyl alcohol and 116 mg of 2-tosyloxymethyl-3,4-dihydro-2H-pyran.

Infrared Absorption Spectrum (liquid film) $\nu_{max}$cm$^{-1}$: 1600, 1360, 1190, 1180.

Nuclear Magnetic Resonance Spectrum (CDCl$_3$, 60 MHz) δ ppm: 1.1–2.0 (6H, multiplet); 3.19 (2H, doublet, J=7 Hz); 3.3–4.2 (3H, multiplet); 4.50 (1H, broad singlet); 4.83 (1H, triplet, J=7 Hz); 6.9–8.0 (12H, multiplet).

(b) Trans-1-{6-[α-(2,4-dichlorobenzyl)benzyloxy]tetrahydropyran-2-ylmethyl}imidazole Following essentially the same procedure as described in Example 10(b), the sodium salt of imidazole was prepared from 31 mg of imidazole and 18 mg of 55% sodium hydride; and then 160 mg of trans-6-[α-(2,4-dichlorobenzyl)benzyloxy]-2-tosyloxymethyltetrahydropyran and 45 mg of sodium iodide were added thereto. The mixture was stirred at 90°–95° C. for 4 hours and then treated and the product purified essentially as in Example 10(b) to give 73 mg of the title compound in the form of a colourless oil.

Infrared Absorption Spectrum (liquid film) $\nu_{max}$cm$^{-1}$: 1580, 1500, 1470, 1110.

Nuclear Magnetic Resonance Spectrum (CDCl$_3$, 60 MHz) $\delta$ ppm: 1.0–1.9 (6H, multiplet); 2.7–3.3 (3H, multiplet); 3.70 (2H, doublet, J=5 Hz); 4.4–4.8 (2H, multiplet); 6.7–7.5 (11H, multiplet).

(c) Oxalic acid salt

Following essentially the same procedure as in Example 10(c), the oxalic acid salt of trans-1-6-[α-(2,4-dichlorobenzyl)benzyloxy]tetrahydropyran-2-ylmethyl]imidazole, melting at 118°–120° C., was prepared.

EXAMPLE 16

Trans-1-{6-[α-(2,4-dichlorobenzyl)-4-methoxybenzyloxy]tetrahydropyran-2-ylmethyl}imidazole (a) Trans-6-[α-(2,4-dichlorobenzyl)-4-methoxybenzyloxy]-2-tosyloxymethyltetrahydropyran Following essentially the same procedure as described in Example 10(a), 1.148 g of the title compound were prepared, in the form of a syrupy mixture of two isomers, using 748 mg of α-(2,4-dichlorobenzyl)-4-methoxybenzyl alcohol, 644 mg of 2-tosyloxymethyl-3,4-dihydro-2H-pyran and a catalytic amount of phosphorus oxytrichloride.

Infrared Absorption Spectrum (Nujol) $\nu_{max}$cm$^{-1}$: 1615, 1600, 1590, 1560, 1510, 1475, 1455, 1440.

Nuclear Magnetic Resonance Spectrum (CDCl$_3$, 60 MHz) $\delta$ ppm: 0.9–1.90 (6H, multiplet); 2.36 (3H, singlet); 3.00 (2H, multiplet); 3.23–4.00 (3H, multiplet); 3.72 (3H, singlet); 4.23–5.00 (2H, multiplet); 6.60–7.87 (11H, multiplet).

(b) Trans-1-{6-[α-(2,4-dichlorobenzyl)-4-methoxybenzyloxy]tetrahydropyran-2-ylmethyl}imidazole Following essentially the same procedure as described in Example 10(b), 157 mg of the title compound, in the form of a colourless oil, were prepared from 400 mg of trans-6-[α-(2,4-dichlorobenzyl)-4-methoxybenzyloxy]-2-tosyloxymethyltetrahydropyran, 72 mg of imidazole, 46 mg of 55% sodium hydride and 106 mg of sodium iodide.

Infrared Absorption Spectrum (liquid film) $\nu_{max}$cm$^{-1}$: 1615, 1590, 1560, 1510, 1475, 1460, 1440.

Nuclear Magnetic Resonance Spectrum (CDCl$_3$, 60 MHz) $\delta$ ppm: 1.0–2.0 (6H, multiplet); 2.93 (2H, multiplet); 3.03–3.80 (3H, multiplet); 3.73 (3H, singlet); 4.23–4.67 (2H, multiplet); 6.50–7.43 (10H, multiplet).

(c) Nitric acid salt

The nitric acid salt of trans-1-{6-[α-(2,4-dichlorobenzyl)-4-methoxybenzyloxy]tetrahydropyran-2-ylmethyl}imidazole, melting at 144°–146° C., was prepared essentially as described in Example 2(c).

EXAMPLE 17

Trans-1-{6-[α-(2,4-dichlorobenzyl)-4-methoxybenzyloxy]tetrahydropyran-2-ylmethyl}-1H-1,2,4-triazole 97.5 mg of 1,2,4-triazole and 62 mg of 55% sodium hydride, 142 mg of sodium iodide, 533 mg of trans-6-[α-(2,4-dichlorobenzyl)-4-methoxybenzyloxy]-2-tosyloxymethyltetrahydropyran and 6 ml of dimethylformamide were reacted and treated essentially as described in Example 3(b) and then the product was purified by column chromatography through silica gel eluted with a 1:2 by volume mixture of benzene and ethyl acetate, to give 244 mg of an isomer of lesser polarity, 109 mg of an isomer of greater polarity and 52 mg of a mixture of the two isomers (in which the ratio of the isomers of lesser to greater polarity was about 2:1).

Isomer of Lesser Polarity

Infrared Absorption Spectrum (liquid film) $\nu_{max}$cm$^{-1}$: 1615, 1590, 1545, 1515, 1475, 1440.

Nuclear Magnetic Resonance Spectrum (CDCl$_3$, 60 MHz) $\delta$ ppm: 0.83–2.0 (6H, multiplet); 2.92 (2H, doublet, J=7 Hz); 3.13 (1H, multiplet); 3.70 (3H, singlet); 3.90 (2H, doublet, J=5 Hz); 4.33 (1H, triplet, J=7 Hz); 4.48 (1H, broad singlet); 6.60–7.30 (7H, multiplet); 7.83 (1H, singlet); 7.95 (1H, singlet).

Isomer of Greater Polarity

Infrared Absorption Spectrum (liquid film) $\nu_{max}$cm$^{-1}$: 1615, 1590, 1560, 1510, 1475, 1440.

Nuclear Magnetic Resonance Spectrum (CDCl$_3$, 60 MHz) $\delta$ ppm: 0.83–2.0 (6H, multiplet); 2.80–3.30 (2H, multiplet); 3.03–3.90 (1H, multiplet); 3.73 (3H, singlet); 4.27–4.65 (1H, multiplet); 4.57 (1H, broad singlet); 6.60–7.30 (7H, multiplet); 7.67 (1H, singlet); 7.75 (1H, singlet).

EXAMPLES 18–26

The following compounds were synthesized by essentially the same procedure as described in Examples 14–17.

EXAMPLE 18

Trans-1-[6-(α-benzyl-2,4-dichlorobenzyloxy)tetrahydropyran-2-ylmethyl]imidazole

Infrared Absorption Spectrum (liquid film) $\nu_{max}$cm$^{-1}$: 3100, 3080, 3050, 1590, 1560, 1500, 1470, 1440.

Nuclear Magnetic Resonance Spectrum (CDCl$_3$, 60 MHz) $\delta$ ppm: 0.93–1.97 (6H, multiplet); 2.54–3.12 (3H, multiplet); 3.50 (2H, doublet, J=6 Hz); 4.48 (1H, broad singlet); 4.98 (1H, doublet of doublets, J=9 and 4 Hz); 6.78 (1H, singlet); 7.00 (1H, singlet); 7.06–7.58 (9H, multiplet).

EXAMPLE 19

Trans-1-{6-[α-(2,4-dichlorobenzyl)-4-chlorobenzyloxy]tetrahydropyran-2-ylmethyl}imidazole Infrared Absorption Spectrum (liquid film) $\nu_{max}$cm$^{-1}$: 1590, 1500, 1485, 1470, 1440, 1410.

Nuclear Magnetic Resonance Spectrum (CDCl$_3$, 60 MHz) $\delta$ ppm: 0.80–2.0 (6H, multiplet); 2.98 (2H, doublet, J=7 Hz); 2.72–3.30 (1H, multiplet); 3.70 (2H, doublet, J=5 Hz); 4.50 (1H, triplet, J=7 Hz); 4.53 (1H, broad singlet); 6.82 (1H, singlet); 7.0–7.5 (9H, multiplet).

EXAMPLE 20

Trans-1-{6-[α-(2,4-dichlorobenzyl)-2,6-dichlorobenzyloxy]tetrahydropyran-2-ylmethyl}imidazole Infrared Absorption Spectrum (liquid film) $\nu_{max}$cm$^{-1}$: 1585, 1565, 1505, 1475, 1440.

Nuclear Magnetic Resonance Spectrum (CDCl$_3$, 60 MHz) $\delta$ ppm: 1.0–2.0 (6H, multiplet); 3.07 (1H, doublet of doublets, J=13 and 6 Hz); 3.60 (1H, doublet of doublets, J=13 and 9 Hz); 4.48 (1H, broad singlet); 5.53 (1H, doublet of doublets, J=9 and 6 Hz); 6.82 (1H, singlet); 6.97–7.47 (8H, multiplet).

EXAMPLE 21

Trans-1-{6-[α-(2,6-dichlorobenzyl)-2,4-dichlorobenzyloxy]tetrahydropyran-2-ylmethyl}imidazole Infrared Absorption Spectrum (liquid film) $\nu_{max}$ cm$^{-1}$: 1590, 1560, 1500, 1465, 1440.

Nuclear Magnetic Resonance Spectrum (CDCl$_3$, 60 MHz) δ ppm: 0.73–2.0 (6H, multiplet); 3.14 (1H, doublet of doublets, J=13 and 5 Hz); 3.42 (1H, doublet of doublets, J=13 and 9 Hz); 3.63 (2H, doublet, J=5.5 Hz); 4.42 (1H, broad singlet); 5.35 (1H, doublet of doublets, J=9 and 5.5 Hz).

EXAMPLE 22

Trans-1-{6-[α-(2,4-dichlorobenzyl)-2,4-dichlorobenzyloxy]tetrahydropyran-2-ylmethyl}imidazole Infrared Absorption Spectrum (liquid film) $\nu_{max}$cm$^{-1}$: 1590, 1560, 1050.

Nuclear Magnetic Resonance Spectrum (CDCl$_3$, 60 MHz) δ ppm: 0.9–1.8 (6H, multiplet); 3.00 (2H, doublet, J=7 Hz); 3.5–4.0 (3H, multiplet); 4.47 (1H, broad singlet); 5.10 (1H, triplet, J=7 Hz); 6.7–7.5 (9H, multiplet).

EXAMPLE 23

Trans-1-{6-[α-(4-fluorobenzyl)-4-chlorobenzyloxy]tetrahydropyran-2-ylmethyl}imidazole

Isomer of Lesser Polarity

Infrared Absorption Spectrum (liquid film) $\nu_{max}$cm$^{-1}$: 1600, 1510, 1490, 1220, 1120.

Nuclear Magnetic Resonance Spectrum (CDCl$_3$, 60 MHz) δ ppm: 1.0–2.0 (6H, multiplet); 2.60 (1H, doublet of doublets, J=6 and 14 Hz); 2.80 (1H, doublet of doublets, J=8 and 14 Hz); 2.8–3.2 (1H, multiplet); 3.57 (2H, doublet, J=6 Hz); 4.10 (1H, doublet of doublets, J=6 and 8 Hz); 4.43 (1H, broad singlet); 6.7–7.5 (11H, multiplet).

Isomer of Greater Polarity

Infrared Absorption Spectrum (liquid film) $\nu_{max}$cm$^{-1}$: 1500, 1220.

Nuclear Magnetic Resonance Spectrum (CDCl$_3$, 60 MHz) δ ppm: 0.9–1.8 (6H, multiplet); 2.6–3.0 (2H, multiplet); 3.43 (2H, broad singlet); 3.1–4.0 (1H, multiplet); 4.2–4.8 (2H, multiplet); 6.7–7.4 (11H, multiplet).

EXAMPLE 24

Trans-1-{6-[α-(4-fluorobenzyl)-4-chlorobenzyloxy]tetrahydropyran-2-ylmethyl}-1H-1,2,4-triazole Infrared Absorption Spectrum (liquid film) $\nu_{max}$cm$^{-1}$: 1600, 1500, 1220.

Nuclear Magnetic Resonance Spectrum (CDCl$_3$, 60 MHz) δ ppm: 1.0–2.0 (6H, multiplet); 2.6–3.0 (2H, multiplet); 3.4–4.2 (3H, multiplet); 4.35 (1H, triplet, J=7 Hz); 4.60 (1H, singlet); 6.7–8.0 (10H, multiplet).

EXAMPLE 25

Trans-1-{6-[α-(2,4-dichlorobenzyl)-2-methoxybenzyloxy]tetrahydropyran-2-ylmethyl}imidazole Infrared Absorption Spectrum (Nujol) $\nu_{max}$cm$^{-1}$: 1605, 1590, 1540, 1505, 1490, 1475, 1440.

Nuclear Magnetic Resonance Spectrum (CDCl$_3$, 60 MHz) δ ppm: 1.0–1.9 (6H, multiplet); 3.0 (2H, doublet, J=6 Hz); 3.40–3.90 (3H, multiplet); 3.83 (3H, singlet); 4.60 (1H, singlet); 5.02 (1H, triplet, J=6 Hz); 6.70–7.50 (10H, multiplet).

EXAMPLE 26

Trans-1-{6-[α-(2-thienyl)-2,4-dichlorophenethyloxy]tetrahydropyran-2-ylmethyl}imidazole Infrared Absorption Spectrum (liquid film) $\nu_{max}$cm$^{-1}$: 1670, 1640, 1590, 1500, 1120.

Nuclear Magnetic Resonance Spectrum (CDCl$_3$, 60 MHz) δ ppm: 0.9–1.8 (6H, multiplet); 2.8–3.3 (3H, multiplet); 3.4–3.8 (2H, multiplet); 4.5–5.0 (2H, multiplet); 6.5–7.4 (9H, multiplet).

EXAMPLE 27

Trans-1-[6-(α,α-dimethyl-2,4-dichlorobenzyloxy)tetrahydropyran-2-ylmethyl]imidazle 98 mg of 55% sodium hydride were added to 5 ml of a dimethylformamide solution containing 153 mg of imidazole and the mixture was stirred at 80° C. for 30 minutes. 2 ml of a dimethylformamide solution containing 710 mg of trans-6-(α,α-dimethyl-2,4-dichlorobenzyloxy)-2-tosyloxymethyltetrahydropyran were then added and the mixture was heated at 85° C. for 2 hours. The reaction mixture was then poured into water and extracted with diethyl ether. The ethereal extract was washed with water, dried over anhydrous sodium sulphate and then concentrated by evaporation under reduced pressure. Purification of the residue by column chromatography through silica gel eluted with a 30:1 by volume mixture of ethyl acetate and triethylamine gave 423 mg of the title compound in the form of a colourless oil.

Infrared Absorption Spectrum (liquid film) $\nu_{max}$cm$^{-1}$: 1590, 1510, 1110, 990.

Nuclear Magnetic Resonance Spectrum (CDCl$_3$, 60 MHz) δ ppm: 1.43 (3H, singlet); 1.50 (3H, singlet); 1.0–2.1 (6H, multiplet); 3.6–4.3 (3H, multiplet); 4.85 (1H, broad singlet); 6.95 (2H, doublet, J=6 Hz); 7.1–7.6 (4H, multiplet).

EXAMPLE 28

1-{Trans-β-[6-(2,4-dichlorobenzyloxy)tetrahydropyran-2-ylmethoxy]phenethyl}imidazole A solution of 106 mg of 1-phenyl-2-(1-imidazolyl)ethanol in 1 ml of dimethylformamide was stirred with 5 mg of 55% sodium hydride at 50° C. for 30 minutes and the mixture was then left to cool at room temperature. To the resulting mixture were added 3 ml of a dimethylformamide solution containing 300 mg of trans-6-(2,4-dichlorobenzyloxy)-2-tosyloxymethyltetrahydropyran, prepared as described in Example 2(a); the mixture was then stirred at 80° C. for 4 hours and then at 90° C. for 1 hour. At the end of this time, the reaction mixture was cooled, poured into water and extracted with diethyl ether. The ethereal extract was washed with water, dried over anhydrous sodium sulphate and then concentrated to evaporation under reduced pressure. The residue was purified by column chromatography through silica gel eluted with a 30:1 by volume mixture of ethyl acetate and triethylamine, to give 107 mg of the title compound as a liquid.

Infrared Absorption Spectrum (liquid film) $\nu_{max}$cm$^{-1}$: 1590, 1500, 1120, 1030.

Nuclear Magnetic Resonance Spectrum (CDCl$_3$, 60 MHz) δ ppm: 1.2–2.1 (6H, multiplet); 3.25–3.5 (2H, multiplet); 3.7–4.3 (3H, multiplet); 4.35–4.90 (3H, multiplet); 5.00 (1H, broad singlet); 6.8–7.7 (11H, multiplet).

(b) 1-{cis-β-[6-(2,4-dichlorobenzyloxy)tetrahydropyran-2-ylmethoxy]phenethyl}imidazole 1 ml of a dimethylformamide solution containing 23 mg of 1-phenyl-2-(1-imidazolyl)ethanol was heated at 50° C. for 30 minutes with 5 mg of 55% sodium hydride, and then 1 ml of a dimethylformamide solution containing 65 mg of cis-6-(2,4-dichlorobenzyloxy)-2-tosyloxymethyltetrahydropyran, prepared as described in Example 2(a), were added thereto. The mixture was heated at 85° C. for 3 hours and then the mixture was treated and the product purified essentially as described in (a) above, to give 20 mg of the title compound as a liquid.

Infrared Absorption Spectrum (liquid film) $\nu_{max}$cm$^{-1}$: 1590, 1560, 1500, 1100, 1080.

Nuclear Magnetic Resonance Spectrum (CDCl$_3$, 60 MHz) δ ppm: 1.1–2.2 (6H, multiplet); 3.2–3.8 (3H, multiplet); 3.9–4.3 (2H, multiplet); 4.3–5.2 (4H, multiplet); 6.9–7.7 (11H, multiplet).

EXAMPLES 29–33

The following compounds were prepared following essentially the same procedures as described in Example 28.

EXAMPLE 29

1-{Trans-β-[6-(2,4-dichlorophenoxy)tetrahydropyran-2-yl-methoxy]phenethyl}imidazole Infrared Absorption Spectrum (liquid film) $\nu_{max}$cm$^{-1}$: 1470, 1240, 1100, 1040.

Nuclear Magnetic Resonance Spectrum (CDCl$_3$, 60 MHz) δ ppm: 1.2–2.2 (6H, multiplet); 3.0–3.6 (2H, multiplet); 4.05 (2H, doublet, J=5 Hz); 3.7–4.3 (1H, multiplet); 4.43 (1H, triplet, J=5 Hz); 5.57 (1H, broad singlet); 6.90 (2H, doublet, J=11 Hz); 7.1–7.55 (9H, multiplet).

1-{Cis-β-[6-(2,4-dichlorophenoxy)tetrahydropyran-2-yl-methoxy]phenethyl}imidazole Infrared Absorption Spectrum (liquid film) $\nu_{max}$cm$^{-1}$: 1590, 1570, 1500, 1480.

Nuclear Magnetic Resonance Spectrum (CDCl$_3$, 60 MHz) δ ppm: 1.1–2.28 (6H, multiplet); 3.36 (2H, doublet, J=5 Hz); 4.03 (2H, doublet, J=6 Hz); 3.64 (1H, multiplet); 4.52 (1H, multiplet); 5.03 (1H, multiplet); 6.7–7.5 (11H, multiplet).

EXAMPLE 30

1-{Trans-β-[6-(2,4-dichlorobenzyloxy)tetrahydropyran-2-ylmethoxy]-4-chlorophenethyl}imidazole Infrared Absorption Spectrum (liquid film) $\nu_{max}$cm$^{-1}$: 1595, 1560.

Nuclear Magnetic Resonance Spectrum (CDCl$_3$, 60 MHz) δ ppm: 1.0–2.0 (6H, multiplet); 3.0–4.8 (9H, multiplet); 4.9 (1H, broad singlet); 6.70–7.46 (10H, multiplet).

EXAMPLE 31

1-{Trans-β-[6-(2,6-dichlorobenzyloxy)tetrahydropyran-2-ylmethoxy]-4-chlorophenethyl}imidazole Infrared Absorption Spectrum (liquid film) $\nu_{max}$cm$^{-1}$: 1600, 1585, 1565.

Nuclear Magnetic Resonance Spectrum (CDCl$_3$, 60 MHz) δ ppm: 1.0–1.8 (6H, multiplet); 3.08–5.05 (9H, multiplet); 6.75–7.45 (10H, multiplet).

EXAMPLE 32

1-{Trans-β-[6-(2,4-dichlorobenzyloxy)tetrahydropyran-2-ylmethoxy]-2,4-dichlorophenethyl}imidazole Infrared Absorption Spectrum (liquid film) $\nu_{max}$cm$^{-1}$: 1595, 1560, 1470, 1100, 1040.

Nuclear Magnetic Resonance Spectrum (CDCl$_3$, 60 MHz) δ ppm: 1.1–2.0 (6H, multiplet); 3.3 (2H, multiplet); 3.6–4.3 (3H, multiplet); 4.63 (2H, AB-quartet, J=14 Hz); 4.8–5.1 (2H, multiplet); 6.7–7.6 (9H, multiplet).

EXAMPLE 33

1-{Trans-β-[6-(2,6-dichlorobenzyloxy)tetrahydropyran-2-ylmethoxy]-2,4-dichlorophenethyl}imidazole Infrared Absorption Spectrum (liquid film) $\nu_{max}$cm$^{-1}$: 1590, 1560, 1110.

Nuclear Magnetic Resonance Spectrum (CDCl$_3$, 60 MHz) δ ppm: 1.1–1.9 (6H, multiplet); 3.27 (2H, doublet, J=4 Hz); 3.7–4.3 (3H, multiplet); 4.4–5.2 (4H, multiplet); 6.8–7.5 (9H, multiplet);

EXAMPLE 34

1-{Trans-β-[6-(2,4-dichlorophenoxymethyl)tetrahydropyran-2-yloxy]phenethyl}imidazole (a) Trans-6-(2,4-dichlorophenoxymethyl)-2-(2-tosyloxy-1-phenylethoxy)tetrahydropyran A solution of 359 mg of 2,4-dichlorophenol in 3 ml of dimethylformamide was stirred with 96 mg of 55% sodium hydride at room temperature for 30 minutes. A solution of 536 mg of 2-tosyloxymethyl-3,4-dihydro-2H-pyran in 2 ml of dimethylformamide was then added, and the mixture was heated at 80°–90° C. for 2 hours. The reaction mixture was then cooled and poured onto a mixture of ice and sodium bicarbonate. The mixture was extracted with diethyl ether and the extract was dried over anhydrous potassium carbonate. After evaporation of the solvent, the residue was purified by column chromatography through silica gel eluted with a 1:2 by volume mixture of benzene and hexane, to give 394 mg of 2-(2,4-dichlorophenoxymethyl)-3,4-dihydro-2H-pyran.

To a solution of 390 mg of this 2-(2,4-dichlorophenoxymethyl)-3,4-dihydro-2H-pyran and 484 mg of α-tosyloxymethylbenzyl alcohol in 8 ml of diethyl ether was added one drop of phosphorus oxytrichloride, and the mixture was stirred at room temperature for 2 days. 3 drops of triethylamine were then added to the mixture and the solvent was evaporated off. The residue was purified by column chromatography through silica gel eluted with a 10:10:1 by volume mixture of benzene, hexane and ethyl acetate, to give 307 mg of an isomer of lesser polarity, 245 mg of an isomer of greater polarity and 170 mg of a mixture thereof of trans-6-(2,4-dichlorophenoxymethyl)-2-(2-tosyloxy-1-phenylethoxy) tetrahydropyran.

Isomer of Lesser Polarity

Infrared Absorption Spectrum (liquid film) $\nu_{max}$cm$^{-1}$: 1600, 1590, 1485, 1450.

Nuclear Magnetic Resonance Spectrum (CDCl$_3$, 60 MHz) δ ppm: 1.32–2.0 (6H, multiplet); 2.40 (3H, singlet); 3.83–4.50 (5H, multiplet); 4.72 (1H, broad singlet); 5.06 (1H, doublet of doublets, J=5 and 9 Hz); 6.64–7.47 (10H, multiplet); 7.73 (2H, doublet, J=8 Hz).

Isomer of Greater Polarity

Infrared Absorption Spectrum (liquid film) $v_{max}$cm$^{-1}$: 1595, 1585, 1480, 1450.

Nuclear Magnetic Resonance Spectrum (CDCl$_3$, 60 MHz) δ ppm: 1.10–2.0 (6H, multiplet); 2.42 (3H, singlet); 3.60 (2H, singlet); 4.10 (2H, doublet, J=6 Hz); 4.08 (1H, multiplet); 4.86 (1H, triplet, J=6 Hz); 5.64 (1H, broad singlet); 6.30–7.47 (10H, multiplet); 7.72 (2H, doublet, J=8 Hz).

(b) 1-{Trans-β-[6-(2,4-dichlorophenoxymethyl)tetrahydropyran-2-yloxy]phenethyl}imidazole (ii) Isomer of Lesser Polarity To a solution of 57 mg of imidazole in 2 ml of dimethylformamide were added 36 mg of 55% sodium hydride, and the mixture was stirred at 70°–80° C. for 30 minutes. The mixture was then left to cool to room temperature, after which a solution of 306 mg of the isomer of lesser polarity of trans-6-(2,4-dichlorophenoxymethyl)-2-(2-tosyloxy-1-phenyl)ethoxytetrahydropyran in 1 ml of dimethylformamide was added, and the mixture was stirred at 80°–90° C. for 2.5 hours. The reaction mixture was then poured into water and extracted with diethyl ether. The extract was washed with water and dried over anhydrous potassium carbonate. After evaporation of the solvent, the residue was purified by column chromatography through silica gel eluted with a 40:11 by volume mixture of ethyl acetate and triethylamine, to give 127 mg of the title compound, melting at 106°–107° C.

Infrared Absorption Spectrum (film) $v_{max}$cm$^{-1}$: 1585, 1570, 1495, 1485, 1430.

Nuclear Magnetic Resonance Spectrum (CDCl$_3$, 60 MHz) δ ppm: 1.1–2.0 (6H, multiplet); 3.0–3.47 (1H, multiplet); 3.80 (2H, doublet, J=5 Hz); 4.17 (2H, doublet, J=6 Hz); 4.72 (1H, broad singlet); 5.10 (1H, triplet, J=6 Hz); 6.73–7.70 (11H, multiplet).

(ii) Isomer of Greater Polarity

To a solution of 45 mg of imidazole in 1.5 ml of dimethylformamide were added 28.7 mg of 55% sodium hydride, and the mixture was stirred at 70°–80° C. for 30 minutes. A solution of 242 mg of the isomer of greater polarity of trans-6-(2,4-dichlorophenoxymethyl)-2-(2-tosyloxy-1-phenyl)ethoxytetrahydropyran in 1 ml of dimethylformamide was then added, and the mixture was stirred at 80°–90° C. for 2.5 hours. The reaction mixture was then treated and the product purified similarly as described in b(i) above, to give 98 mg of the title compound, in the form of a colourless oil.

Infrared Absorption Spectrum (liquid film) $v_{max}$cm$^{-1}$: 1585, 1570, 1495, 1480, 1445.

Nuclear Magnetic Resonance Spectrum (CDCl$_3$, 60 MHz) δ ppm: 1.0–2.05 (6H, multiplet); 3.57 (2H, singlet); 3.65–4.08 (1H, multiplet); 4.10 (2H, doublet, J=6 Hz); 4.58 (1H, broad singlet); 4.80 (1H, triplet, J=6 Hz); 6.40–7.47 (11H, multiplet).

EXAMPLE 35

1-{Trans-β-[6-(2,4-dichlorophenoxymethyl)tetrahydropyran-2-yloxy]-2,4-dichlorophenethyl}imidazole (a) Trans-6-(2,4-dichlorophenoxymethyl)-2-[2-bromo-1-(2,4-dichlorophenyl)ethoxy]tetrahydropyran To 10 ml of an ethereal solution of 425 mg of α-bromomethyl-2,4-dichlorobenzyl alcohol and 340 mg of 2-(2,4-dichlorophenoxymethyl)-3,4-dihydro-2H-pyran was added a catalytic amount (2 drops) of phosphorus oxytrichloride, and the mixture was stirred at room temperature for 4 days. 3 drops of triethylamine were then added and the solvent was evaporated off under reduced pressure. The residue was purified by column chromatography through silica gel eluted with a 40:2:1 by volume mixture of hexane, benzene and ethyl acetate, to give 681 mg of the isomer of lesser polarity of trans-6-(2,4-dichlorophenoxymethyl)-2-[2-bromo-1-(2,4-dichlorophenyl)ethoxy]tetrahydropyran as colorless crystals melting at 104°–105° C.

Nuclear Magnetic Resonance Spectrum (CDCl$_3$, 60 MHz) δ ppm: 1.5–2.2 (6H, multiplet); 3.60 (2H, doublet of doublets, J=4 and 7 Hz); 4.0 (2H, AB-doublet, J=5 Hz); 4.3–4.8 (1H, multiplet); 4.67 (1H, broad singlet); 5.30 (1H, doublet of doublets, J=4 and 7 Hz); 6.65–7.5 (6H, multiplet).

(b) 1-{Trans-β-[6-(2,4-dichlorophenoxymethyl)tetrahydropyran-2-yloxyl]-2,4-dichlorophenethyl}imidazole A mixture of 163 mg of imidazole, 317 mg of the isomer of lesser polarity of trans-6-(2,4-dichlorophenoxymethyl)-2-[2-bromo-1-(2,4-dichlorophenyl)ethoxy]tetrahydropyran and 180 mg of sodium iodide in 5 ml of dimethylformamide was stirred whilst heating at 130° C. for 10 hours, and then treated and purified as in Example 34(b)(i), to give 136 mg of the isomer of lesser polarity of the title compound, as a colourless oil.

Infrared Absorption Spectrum (liquid film) $v_{max}$cm$^{-1}$: 1590, 1480, 1290, 1040.

Nuclear Magnetic Resonance Spectrum (CDCl$_3$, 60 MHz) δ ppm; 1.1–2.0 (6H, multiplet); 3.0–3.5 (1H, multiplet); 3.80 (2H, AB-doublet, J=4 Hz); 4.12 (1H, doublet, J=8 Hz); 4.18 (1H, doublet, J=4 Hz); 4.65 (1H, broad singlet); 5.40 (1H, doublet of doublets, J=4 and 8 Hz); 6.6–7.6 (9H, multiplet).

EXAMPLE 36

1-{Trans-β-[6-(2,4-dichlorophenoxymethyl)tetrahydropyran-2-yloxy]-4-chlorophenethyl}imidazole (a) Trans-6-(2,4-dichlorophenoxymethyl)-2-[2-bromo-1-(4-chlorophenyl)ethoxy]tetrahydropyran To a solution of 259 mg of α-bromomethyl-4-chlorobenzyl alcohol and 311 mg of 2-(2,4-dichlorophenoxymethyl)-3,4-dihydro-2H-pyran in 6 ml of diethyl ether was added one drop of phosphorus oxytrichloride, and the mixture was stirred at room temperature for 1 day. After 3 drops of triethylamine had been added, the solvent was evaporated off under reduced pressure and the residue was purified by column chromatography through silica gel eluted with a 5:50:11 by volume mixture of benzene, hexane and ethyl acetate, to give 147 mg of the isomer of lesser polarity of trans-6-(2,4-dichlorophenoxymethyl)-2-[2-bromo-1-(4-chlorophenyl)ethoxy]tetrahydropyran melting at 86°–87° C., 165 mg of the isomer of greater polarity melting at 97°–98° C., and 80 mg of a mixture thereof.

Isomer of Lesser Polarity

Infrared Absorption Spectrum (Nujol) $v_{max}$cm$^{-1}$: 1600, 1595, 1570

Nuclear Magnetic Resonance Spectrum (CDCl$_3$, 60 MHz) δ ppm: 1.15–2.10 (6H, multiplet); 3.55 (1H, doublet, J=6 Hz); 3.58 (1H, doublet, J=7.5 Hz); 3.98 (2H, doublet, J=5.5 Hz); 4.47 (1H, multiplet); 4.66 (1H, broad singlet); 4.98 (1H, doublet of doublets, J=7.5 and 5.5 Hz); 6.72–7.50 (7H, multiplet).

Isomer of Greater Polarity

Infrared Absorption Spectrum (Nujol) $\nu_{max}$cm$^{-1}$: 1600, 1590, 1575.

Nuclear Magnetic Resonance Spectrum (CDCl$_3$, 60 MHz) δ ppm: 1.15–2.10 (6H, multiplet); 3.50 (1H, doublet, J=6 Hz); 3.63 (2H, singlet); 3.80 (1H, multiplet); 3.83 (1H, triplet, J=6 Hz); 5.17 (1H, broad singlet); 6.45–7.40 (7H, multiplet).

(b) 1-{Trans-β-[6-dichlorophenoxymethyl)tetrahydropyran-2-yloxy]-4-chlorophenethyl}imidazole (i) Isomer of Lesser Polarity A mixture of 116 mg of imidazole, 212 mg of the isomer of lesser polarity of trans-6-(2,4-dichlorophenoxymethyl)-2-[2-bromo-1-(4-chlorophenyl)ethoxy]tetrahydropyran and 128 mg of sodium iodide in 4 ml of dimethylformamide was stirred, whilst heating at 130°–140° C., for 10 hours. After this, essentially the same treatment and purification procedures as described in Example 34(b)(i) were performed, to give 28 mg of the title compound, as a colourless oil.

Infrared Absorption Spectrum (liquid film) $\nu_{max}$cm$^{-1}$: 1590, 1580, 1560.

Nuclear Magnetic Resonance Spectrum (CDCl$_3$, 60 MHz) δ ppm: 1.06–2.10 (6H, multiplet); 3.24 (1H, multiplet); 3.74 (2H, doublet, J=5 Hz); 4.08 (2H, doublet, J=6 Hz); 4.60 (1H, broad singlet); 5.00 (1H, triplet, J=6 Hz); 6.60–7.67 (10H, multiplet).

(ii) Isomer of Greater Polarity

A solution of 60 mg of imidazole, 110 mg of the isomer of greater polarity of trans-6-(2,4-dichlorophenoxymethyl)-2-[2-bromo-1-(4-chlorophenyl)ethoxy]tetrahydropyran and 66 mg of sodium iodide in 2 ml of dimethylformamide was heated at 130°–140° C. for 10 hours, after which it was subjected to treatment and purification similar to that described in Example 34(b)(i), to give 50 mg of the title compound as a colourless oily liquid.

Nuclear Magnetic Resonance Spectrum (CDCl$_3$, 60 MHz) δ ppm: 1.15–2.0 (6H, multiplet); 3.62 (2H, singlet); 3.72 (1H, multiplet); 4.10 (2H, doublet, J=6 Hz); 4.66 (1H, broad singlet); 4.85 (1H, triplet, J=6 Hz); 6.47–7.55 (10H, multiplet).

EXAMPLE 37

1-{Trans-β-[6-(4-fluorophenoxymethyl)tetrahydropyran-2-yloxy]-2,4-dichlorophenethyl}imidazole (a) Trans-6-(4-fluorophenoxymethyl)-2-[2-bromo-1-(2,4-dichlorophenyl)ethoxy]tetrahydropyran A mixture of a solution of 247 mg of p-fluorophenol in 1 ml of dimethylformamide with 87 mg of 55% sodium hydride was stirred at room temperature for 30 minutes. 537 mg of 2-tosyloxymethyl-3,4-dihydro-2H-pyran were then added to the mixture, which was allowed to react at 90° C. for 3 hours. Thereafter, the mixture was treated and the product purified essentially as described in Example 34(a) to give 102 mg of 2-(4-fluorophenoxymethyl)-3,4-dihydro-2H-pyran as a colourless oil.

389 mg of α-bromomethyl-2,4-dichlorobenzyl alcohol and 300 mg of 2-(4-fluorophenoxymethyl)-3,4-dihydro-2H-pyran, prepared as described above, were dissolved in 10 ml of diethyl ether. A catalytic amount (2 drops) of phosphorus oxytrichloride was added to the resulting solution and the mixture allowed to react at room temperature for 4 days, after which it was treated and the product purified essentially as described in Example 34(a), to give 214 mg of the isomer of lesser polarity of trans-6-(4-fluorophenoxymethyl)-2-[2-bromo-1-(2,4-dichlorophenyl)ethoxy]tetrahydropyran, 211 mg of the isomer of greater polarity and 143 mg of a mixture of these isomers.

Isomer of Lesser Polarity

Infrared Absorption Spectrum (liquid film) $\nu_{max}$cm$^{-1}$: 1590, 1500, 1220.

Nuclear Magnetic Resonance Spectrum (CDCl$_3$, 60 MHz) δ ppm: 1.2–2.2 (6H, multiplet); 3.60 (1H, doublet, J=7 Hz); 3.63 (1H, doublet, J=4 Hz); 3.95 (2H, doublet, J=5 Hz); 4.3–4.8 (1H, multiplet); 4.73 (1H, broad singlet); 5.38 (1H, doublet of doublets, J=4 and 7 Hz); 6.7–7.6 (7H, multiplet).

Isomer of Greater Polarity

Infrared Absorption Spectrum (liquid film) $\nu_{max}$cm$^{-1}$: 1590, 1510, 1225, 1210.

Nuclear Magnetic Resonance Spectrum (CDCl$_3$, 60 MHz) δ ppm: 1.1–2.2 (6H, multiplet); 3.25–4.00 (5H, multiplet); 5.1–5.5 (2H, multiplet); 6.5–7.7 (7H, multiplet).

(b) 1-{Trans-β-[6-(4-fluorophenoxymethyl)tetrahydropyran-2-yloxy]-2,4-dichlorophenethyl}imidazole (i) Isomer of Lesser Polarity A mixture of 120 mg of imidazole, 212 mg of the isomer of lesser polarity of trans-6-(4-fluorophenoxymethyl)-2-[2-bromo-1-(2,4-dichlorophenyl)ethoxy]tetrahydropyran and 133 mg of sodium iodide in 5 ml of dimethylformamide was stirred at 130° C. for 9 hours. At the and of this time, the mixture was treated and the product purified essentially as described in Example 34(b)(i), to give 108 mg of the title compound in the form of a colourless oil.

Infrared Absorption Spectrum (liquid film) $\nu_{max}$cm$^{-1}$: 1580, 1500, 1200.

Nuclear Magnetic Resonance Spectrum (CDCl$_3$, 60 MHz) δ ppm: 1.4–2.0 (6H, multiplet); 2.9–3.4 (1H, multiplet); 3.73 (2H, doublet, J=5 Hz); 4.12 (1H, doublet, J=8 Hz); 4.17 (1H, doublet, J=4 Hz); 4.70 (1H, broad singlet); 5.40 (1H, doublet of doublets, J=8 and 4 Hz); 6.8–7.7 (10H, multiplet).

(ii) Isomer of Greater Polarity

A mixture of 120 mg of imidazole, 210 mg of the isomer of greater polarity of trans-6-(4-fluorophenoxymethyl)-2-[2-bromo-1-(2,4-dichlorophenyl)ethoxy]tetrahydropyran and 132 mg of sodium iodide in 5 ml of dimethylformamide was stirred at 130° C. for 9 hours, and then the mixture was treated and the product purified essentially as described in Example 34(b)(i), to give 106 mg of the title compound.

Infrared Absorption Spectrum (liquid film) $\nu_{max}$cm$^{-1}$: 1590, 1500, 1200, 1040.

Nuclear Magnetic Resonance Spectrum (CDCl$_3$, 60 MHz) δ ppm: 1.2–2.2 (6H, multiplet); 3.4–4.4 (5H, multiplet); 4.63 (1H, broad singlet); 5.33 (1H, doublet of doublets, J=4 and 7 Hz); 6.5–7.6 (10H, multiplet).

EXAMPLE 38

(a)

Trans-6-(4-chlorobenzyloxymethyl)-2-[bromo-1-(2,4-dichlorophenyl)ethoxy]tetrahydropyran 50 mg of 55% sodium hydride were added to a solution of 193 mg of 4-chlorobenzyl alcohol in 1 ml of dimethylformamide, and the mixture was stirred at room temperature for 30 minutes. A solution of 326 mg of 2-tosyloxymethyl-3,4-dihydro-2H-pyran in 2 ml of dimethylformamide was then added and the resulting mixture was allowed to react at 90° C. for 4 hours. The mixture was then treated and the product purified essentially as described in Example 34(a), to give 82 mg of 2-(4-chlorobenzyloxymethyl)-3,4-dihydro-2H-pyran, as a colourless oil.

102 mg of α-bromomethyl-2,4-dichlorobenzyl alcohol and the 82 mg of 2-(4-chlorobenzyloxymethyl)-3,4-dihydro-2H-pyran prepared above were then dissolved in 2 ml of diethyl ether, and one drop of phosphorus oxytrichloride was then added. The mixture was then allowed to react at room temperature for 4 days, after which it was treated and the product purified essentially as described in Example 34(a), to give 121 mg of trans-6-(4-chlorobenzyloxymethyl)-2-[2-bromo-1-(2,4-dichlorophenyl)ethoxy]tetrahydropyran.

Infrared Absorption Spectrum (liquid film) $\nu_{max}$cm$^{-1}$: 1595, 1565, 1495, 1470, 1440.

Nuclear Magnetic Resonance spectrum (CDCl$_3$, 60 MHz) δ ppm: 1.0–2.3 (6H, multiplet); 3.1–3.85 (5H, multiplet); 4.30, 4.50 (together 2H, singlet); 4.60, 5.10 (together 1H, broad singlet); 5.24 (1H, doublet of doublets, J=4 and 6 Hz); 6.9–7.6 (7H, multiplet).

(b) 1-{Trans-β-[6-(4-chlorobenzyloxymethyl)tetrahydropyran-2-yloxy]-2,4-dichlorophenethyl}imidazole A solution of 121 mg of trans-6-(4-chlorobenzyloxymethyl)-2-[2-bromo-1-(2,4-dichlorophenyl)ethoxy]tetrahydropyran, 73 mg of imidazole and 81 mg of sodium iodide in 3 ml of dimethylformamide was heated, with stirring, at 130°–140° C. for 6 hours, after which the mixture was treated and the product purified essentially as described in Example 34(b)(i), to give 66 mg of the title compound, in the form of a colourless oil.

Infrared Absorption Spectrum (liquid film) $\nu_{max}$cm$^{-1}$: 1590, 1580, 1560, 1500.

Nuclear Magnetic Resonance Spectrum (CDCl$_3$, 60 MHz) δ ppm: 1.13–2.00 (6H, multiplet); 2.75–4.73 (8H, multiplet); 5.35 (1H, multiplet); 6.83–7.57 (10H, multiplet).

EXAMPLE 39

1-{Trans-β-[6-(4-chlorobenzylthiomethyl)tetrahydropyran-2-yloxy]-2,4-dichlorophenethyl}imidazole (a) Trans-6-(4-chlorobenzylthiomethyl)-2-[2-bromo-1-(2,4-dichlorophenyl)ethoxy]tetrahydropyran A solution of 260 mg of 4-chlorobenzyl mercaptan in 3 ml of dimethylformamide was mixed with 72 mg of 55% sodium hydride, and the mixture was stirred at room temperature for 30 minutes. 2 ml of a dimethylformamide solution containing 400 mg of 2-tosyloxymethyl-3,4-dihydro-2H-pyran were then added, and the mixture was stirred at 80°–90° C. for 4 hours. The mixture was then treated and the product purified essentially as described in Example 34(a) to give 224 mg of 2-(4-chlorobenzylthiomethyl)-3,4-dihydro-2H-pyran, as a colourless oil.

2 Drops of phosphorus oxytrichloride were then added to a solution of 261 mg of 2-(4-chlorobenzylthiomethyl)-3,4-dihydro-2H-pyran, prepared as described above, and 261 mg of α-bromomethyl-2,4-dichlorobenzyl alcohol in 5 ml of diethyl ether, and the mixture was allowed to react at room temperature for 4 days, after which it was treated and the product was purified essentially as described in Example 34(a), to give 130 mg of the isomer of smaller polarity of trans-6-(4-chlorobenzylthiomethyl)-2-[2-bromo-1-(2,4-dichlorophenyl)ethoxy]tetrahydropyran and 231 mg of a 1:1 mixture of the isomers of greater and lesser polarity.

Isomer of Lesser Polarity

Infrared Absorption Spectrum (liquid film) $\nu_{max}$cm$^{-1}$: 1595, 1580, 1565, 1490, 1465, 1460, 1440.

Nuclear Magnetic Resonance Spectrum (CDCl$_3$, 60 MHz) δ ppm: 1.10–2.06 (6H, multiplet); 2.46 (2H, doublet, J=6 Hz); 3.56 (1H, doublet, J=7 Hz); 3.60 (1H, doublet, J=4 Hz); 3.76 (2H, singlet); 4.23 (1H, multiplet); 4.65 (1H, broad singlet); 5.40 (1H, doublet of doublets, J=4 and 7 Hz); 7.04–7.57 (7H, multiplet).

(b) 1-{Trans-β-[6-(4-chlorobenzylthiomethyl)tetrahydropyran-2-yloxy]-2,4-dichlorophenethyl}-imidazole 130 mg of the isomer of lesser polarity of trans-6-(4-chlorobenzylthiomethyl)-2-[2-bromo-1-(2,4-dichlorophenyl)ethoxy]tetrahydropyran, 67.5 mg of imidazole and 74 mg of sodium iodide were reacted in dimethylformamide at 130° C. for 9 hours and then treated and the product purified essentially as described in Example 34(b)(i), to give 60 mg of the title compound in the form of a colourless oil.

Infrared Absorption Spectrum (liquid film) $\nu_{max}$cm$^{-1}$: 1590, 1580, 1565, 1510, 1505, 1490, 1470, 1440.

Nuclear Magnetic Resonance Spectrum (CDCl$_3$, 60 MHz) δ ppm: 0.92–1.90 (6H, multiplet); 2.30 (2H, doublet, J=6 Hz); 3.00 (1H, multiplet); 3.67 (2H, singlet); 4.10 (1H, doublet, J=7 Hz); 4.63 (1H, broad singlet); 4.67 (1H, doublet, J=4 Hz); 5.43 (1H, doublet of doublets, J=4 and 7 Hz); 6.82–7.60 (10H, multiplet).

The oxalic acid salt prepared essentially as described in Example 2(e), melted at 135°–137° C.

EXAMPLES 40–47

Following essentially the same procedures as in Examples 34–39, the following compounds were prepared.

EXAMPLE 40

1-{Trans-β-[6-(2-chlorophenoxymethyl)tetrahydropyran-2-yloxy]-2,4-dichlorophenethyl}imidazole Isomer of Lesser Polarity Infrared Absorption Spectrum (liquid film) $\nu_{max}$cm$^{-1}$: 1590, 1580, 1560, 1500, 1485, 1465, 1445.

Nuclear Magnetic Resonance Spectrum (CDCl$_3$, 60 MHz) δ ppm: 1.20–2.10 (6H, multiplet); 3.0–4.27 (5H, multiplet); 4.70 (1H, broad singlet); 5.48 (1H, doublet of doublets, J=4 and 7 Hz); 6.66–7.60 (10H, multiplet).

Mixture of Isomers of Lesser and Greater Polarity

Infrared Absorption Spectrum (liquid film) $\nu_{max}$cm$^{-1}$: 1590, 1580, 1560, 1510, 1500.

Nuclear Magnetic Resonance Spectrum (CDCl$_3$, 60 MHz) δ ppm: 1.16–2.16 (6H, multiplet); 3.0–5.55 (7H, multiplet); 6.50–7.55 (10H, multiplet).

EXAMPLE 41

1-{Trans-β-[6-(4-chlorophenylthiomethyl)tetrahydropyran-2-yloxy]-2,4-dichlorophenethyl}imidazole Isomer of Lesser Polarity Infrared Absorption Spectrum (liquid film) $\nu_{max}$cm$^{-1}$: 1590, 1500, 1470, 1100, 1030.

Nuclear Magnetic Resonance Spectrum (CDCl$_3$, 60 MHz) δ ppm: 1.30–2.00 (6H, multiplet); 2.7–3.3 (3H, multiplet); 4.10 (1H, doublet, J=7 Hz); 4.12 (1H, doublet, J=4 Hz); 4.63 (1H, broad singlet); 5.38 (1H, doublet of doublets, J=4 and 7 Hz); 6.8–7.6 (10H, multiplet).

Isomer of Greater Polarity

Infrared Absorption Spectrum (liquid film) $v_{max}$cm$^{-1}$: 1590, 1560, 1500, 1470, 1100, 1030.

Nuclear Magnetic Resonance Spectrum (CDCl$_3$, 60 MHz) δ ppm: 1.0–2.1 (6H, multiplet); 2.75 (2H, singlet); 3.2–3.7 (1H, multiplet); 4.10 (1H, doublet, J=8 Hz); 4.17 (1H, doublet, J=4 Hz); 4.60 (1H, broad singlet); 5.32 (1H, doublet of doublets, J=4 and 8 Hz); 6.7–7.6 (10H, multiplet).

EXAMPLE 42

1-{Trans-β-[6-(4-fluorophenoxymethyl)tetrahydropyran-2-yloxy]-4-chlorophenethyl}imidazole Isomer of Lesser Polarity Infrared Absorption Spectrum (liquid film) $v_{max}$cm$^{-1}$: 1600, 1510, 1490, 1480, 1410.

Nuclear Magnetic Resonance Spectrum (CDCl$_3$, 60 MHz) δ ppm: 1.30–2.00 (6H, multiplet), 3.20 (1H, multiplet); 3.70 (2H, doublet, J=4 Hz); 4.05 (2H, doublet, J=6 Hz); 4.60 (1H, broad signlet);

4.83 (1H, triplet, J=6 Hz); 6.76–7.52 (11H, multiplet).

EXAMPLE 43

1-{Trans-β-[6-(4-acetamidophenoxymethyl)tetrahydropyran-2-yloxy]-2,4-dichlorophenethyl}imidazole Infrared Absorption Spectrum (liquid film) $v_{max}$cm$^{-1}$: 3250, 1660, 1550, 1510, 1230.

Nuclear Magnetic Resonance Spectrum (CDCl$_3$, 60 MHz) δ ppm: 1.2–2.0 (6H, multiplet); 2.03 (3H, singlet); 3.3–4.4 (5H, multiplet); 4.50, 4.52 (together 1H, broad singlet); 4.9–5.4 (1H, multiplet); 6.4–7.6 (10H, multiplet); 9.37, 9.45 (together 1H, broad singlet).

EXAMPLE 44

1-{Trans-β-[6-(4-acetamidophenoxymethyl)tetrahydropyran-2-yloxy]-4-chlorophenethyl}imidazole Infrared Absorption Spectrum (liquid film) $v_{max}$cm$^{-1}$: 3250, 1660, 1540, 1510, 1230.

Nuclear Magnetic Resonance Spectrum (CDCl$_3$, 60 MHz) δ ppm: 1.3–2.0 (6H, multiplet); 2.0 (3H, singlet); 3.3–4.1 (5H, multiplet); 4.4–5.0 (2H, multiplet); 6.5–7.4 (11H, multiplet); 8.85 (1H, singlet).

EXAMPLE 45

1-{Trans-β-[6-(α-naphthoxymethyl)tetrahydropyran-2-yloxy]-2,4-dichlorophenethyl}imidazole Isomer of Lesser Polarity Infrared Absorption Spectrum (liquid film) $v_{max}$cm$^{-1}$: 1600, 1585, 1565, 1505, 1480, 1470, 1440, 1400.

Nuclear Magnetic Resonance Spectrum (CDCl$_3$, 60 MHz) δ ppm: 1.36–2.40 (6H, multiplet); 3.23 (1H, multiplet); 3.70–4.13 (4H, multiplet); 4.59 (1H, broad singlet); 5.33 (1H, doublet of doublets, J= and Hz); 6.50–8.40 (13H, multiplet).

EXAMPLE 46

1-{Trans-β-[6-(α-naphthyloxymethyl)tetrahydropyran-2-yloxy]-2,4-dichlorophenethyl}-1H-1,2,4-triazole Mixture of Isomers of Lesser and Greater Polarity Infrared Absorption Spectrum (liquid film) $v_{max}$cm$^{-1}$: 1605, 1585, 1510, 1460, 1445.

Nuclear Magnetic Resonance Spectrum (CDCl$_3$, 60 MHz) δ ppm: 1.0–2.6 (6H, multiplet); 3.4–4.3 (5H, multiplet); 5.17–5.90 (2H, multiplet); 6.5–8.3 (12H, multiplet).

EXAMPLE 47

1-{Trans-β-[6-(4-phenylphenoxymethyl)tetrahydropyran-2-yloxy]-2,4-dichlorophenethyl}imidazole Isomer of Lesser Polarity Infrared Absorption Spectrum (liquid film) $v_{max}$cm$^{-1}$: 1610, 1590, 1485.

Nuclear Magnetic Resonance Spectrum (CDCl$_3$, 60 MHz) δ ppm: 1.70 (6H, multiplet); 2.9–3.5 (1H, multiplet); 3.8 (2H, doublet, J=4 Hz); 4.08 (1H, doublet, J=8 Hz); 4.13 (1H, doublet, J=4 Hz); 4.67 (1H, broad singlet); 5.37 (1H, doublet of doublets, J=4 and 8 Hz); 6.8–7.7 (15H, multiplet).

Mixture of Isomers of Lesser and Greater Polarity

Infrared Absorption Spectrum (liquid film) $v_{max}$cm$^{-1}$: 1610, 1580, 1515, 1485.

Nuclear Magnetic Resonance Spectrum (CDCl$_3$, 60 MHz) δ ppm: 1.3–2.1 (6H, multiplet); 3.0–3.6 (1H, multiplet); 3.5–4.3 (4H, multiplet); 4.5–4.8 (1H, multiplet); 5.10–5.55 (1H, multiplet); 6.65–7.7 (15H, multiplet).

EXAMPLE 48

1-{4-(4-chlorophenyl)-trans-2-[6-(2,4-dichlorophenoxymethyl)tetrahydropyran-2-yloxy]butyl}imidazole (a) Trans-6-(2,4-dichlorophenoxymethyl)-2-[1-chloro-4-(4-chlorophenyl)-2-butoxy]tetrahydropyran 2 Drops of phosphorus oxytrichloride were added to a solution of 282 mg of 2-(2,4-dichlorophenoxymethyl)-3,4-dihydro-2H-pyran and 286 mg of 1-chloro-4-(4-chlorophenyl)-2-butanol in 7 ml of diethyl ether, and the mixture was allowed to react at room temperature for 4 days. At the end of this time, 3 drops of triethylamine were added, the solvent was evaporated off and the residue was purified by column chromatography through silica gel eluted with a 30:5:1 by volume mixture of hexane, benzene and ethyl acetate, to give 441 mg of trans-6-(2,4-dichlorophenoxymethyl)-2-[1-chloro-4-(chlorophenyl)-2-butoxy]tetrahydropyran as a pale yellow liquid comprising a mixture of isomers in a ratio of about 1:1.

Infrared Absorption Spectrum (liquid film) $v_{max}$cm$^{-1}$: 1590, 1480, 1300, 1060.

Nuclear Magnetic Resonance Spectrum (CDCl$_3$, 60 MHz) δ ppm: 1.2–2.3 (8H, multiplet); 2.5–3.0 (2H, multiplet); 3.3–4.7 (6H, multiplet); 4.93 (0.5H, broad singlet); 5.07 (0.5H, broad singlet); 6.65–7.50 (7H, multiplet).

(b) 1-{4-(4-Chlorophenyl)-trans-2-[6-(2,4-dichlorophenoxymethyl)tetrahydropyran-2-yloxy]butyl}-imidazole A solution of 90 mg of imidazole and 58 mg of 55% sodium hydride in 2 ml of dimethylformamide was stirred at 80° C. for 30 minutes and then left to cool to room temperature. 2 ml of a dimethylformamide solution containing 420 mg of trans-6-(2,4-dichlorophenoxymethyl)-2-[1-chloro-4-(4-chlorophenyl)-2-butoxy]tetrahydropyran and 132 mg of sodium iodide were then added to the mixture and stirring was continued at 90° C. for 4 hours. The mixture was then treated and the product purified essentially as described in Example 34(b)(i), to give 193 mg of the title compound as a colourless oil containing approximately B 1:1 mixture of isomers.

Infrared Absorption Spectrum (liquid film) $v_{max}cm^{-1}$: 1590, 1480, 1450, 1290, 1060.

Nuclear Magnetic Resonance Spectrum (CDCl$_3$, 60 MHz) δ ppm: 1.1–2.1 (8H, multiplet); 2.4–3.0 (2H, multiplet); 3.2–4.7 (6H, multiplet); 5.00 (0.5H, broad singlet); 5.30 (0.5H, broad singlet); 6.6–7.6 (10H, multiplet).

EXAMPLE 49

1-{4-(2,4-Dichlorophenyl)-trans-2-[6-(2,4-dichlorophenoxymethyl)tetrahydropyran-2-yloxy]butyl}-imidazole (a) Trans-6-(2,4-dichlorophenoxymethyl)-2-[1-chloro-4-(2,4-dichlorophenyl)-2-butoxy]tetrahydropyran 2 Drops of phosphorus oxytrichloride were added to a solution of 388 mg of 2-(2,4-dichlorophenoxymethyl)-3,4-dihydro-2H-pyran and 418 mg of 1-chloro-4-(2,4-dichlorophenyl)-2-butanol in 8 ml of diethyl ether, and the mixture was allowed to react at room temperature for 2 days. At the the end of this time, 3 drops of triethylamine were added and the solvent was evaporated off. The residue was purified by column chromatography through silica gel eluted with a 50:5:1 by volume mixture of hexane, benzene and ethyl acetate, to give 185 mg of the isomer of lesser polarity of trans-6-(2,4-dichlorphenoxymethyl)-2-[1-chloro-4-(2,4-dichlorophenyl)-2-butoxy]tetrahydropyran and 153 mg of the isomer of greater polarity.

Isomer of Lesser Polarity

Infrared Absorption Spectrum (liquid film) $v_{max}cm^{-1}$: 1595, 1560, 1485, 1475, 1445.

Nuclear Magnetic Resonance Spectrum (CDCl$_3$, 60 MHz) δ ppm: 1.05–2.20 (8H, multiplet); 2.72 (2H, doublet of doublets, J=9.5 and 5.5 Hz); 3.80 (2H, singlet); 3.89 (2H, doublet, J=6 Hz); 3.43–4.63 (2H, multiplet); 4.94 (1H, broad singlet); 6.62–7.43 (6H, multiplet).

Isomer of Greater Polarity

Infrared Absorption Spectrum (liquid film) $v_{max}cm^{-1}$: 1595, 1565, 1490, 1455.

Nuclear Magnetic Resonance Spectrum (CDCl$_3$, 60 MHz) δ ppm: 1.16–2.23 (8H, multiplet); 2.78 (2H, multiplet); 3.57 (2H, doublet, J=5 Hz); 3.88 (2H, doublet, J=6 Hz); 3.40–4.62 (2H, multiplet); 5.03 (1H, broad singlet); 6.6–7.4 (6H, multiplet).

(b) 1-{4-(2-4-dichlorophenyl)-trans-2-[6-(2,4-dichlorophenoxymethyl)tetrahydropyran-2-yloxy]-butyl}-imidazole (i) Isomer of Lesser Polarity A solution of 37 mg of imidazole in 1 ml of dimethylformamide was mixed with 24 mg of 55% sodium hydride and stirred at 70°–80° C. for 30 minutes, after which the mixture was left to cool to room temperature. A solution of 185 mg of the isomer of lesser polarity of trans-6-(2,4-dichlorophenoxymethyl)-2-[1-chloro-4-(2,4-dichlorophenyl)-2-butoxy]tetrahydropyran in 1 ml of dimethylformamide was then added, followed by 81 mg of sodium iodide and the mixture was allowed to react at 80°–90° C. for 4 hours. The mixture was then treated and the product purified essentially as described in Example 34(b)(i), to give 92 mg of the title compound, in the form of a colourless oil.

Infrared Absorption Spectrum (liquid film) $v_{max}cm^{-1}$: 1595, 1560, 1500, 1485, 1455.

Nuclear Magnetic Resonance Spectrum (CDCl$_3$, 60 MHz) δ ppm: 1.18–2.20 (8H, multiplet); 2.74 (2H, doublet of doublets, J=9.5 and 5.5 Hz); 3.40 (1H, multiplet); 3.78 (2H, doublet, J=5 Hz); 4.00 (1H, multiplet); 4.10 (2H, singlet); 5.00 (1H, broad singlet); 6.64–7.52 (9H, multiplet).

(ii) Isomer of Greater Polarity 44 mg of imidazole and 28 mg of 55% sodium hydride were stirred in 1 ml of dimethylformamide at 80° C. for 30 minutes, and the mixture was then left to cool to room temperature. A solution of 222 mg of the isomer of greater polarity of trans-6-(2,4-dichlorophenoxymethyl)-2-[1-chloro-4-(2,4-dichlorophenyl)-2-butoxy]tetrahydropyran in 1 ml of dimethylformamide was then added, followed by 97 mg of sodium iodide. The mixture was then heated, with stirring, at 80°–90° C. for 4 hours, after which it was treated and the product was purified essentially as described in Example 34(b)(i), to give 147 mg of the title compound, in the form of a colourless oil.

Infrared Absorption Spectrum (liquid film) $v_{max}cm^{-1}$: 1595, 1565, 1485, 1460.

Nuclear Magnetic Resonance Spectrum (CDCl$_3$, 60 MHz) δ ppm: 1.16–2.20 (8H, multiplet); 2.50–3.00 (2H, multiplet); 3.67–4.40 (4H, multiplet); 4.00 (2H, singlet); 4.59 (1H, broad singlet); 6.63–7.60 (9H, multiplet).

EXAMPLE 50

1-[Trans-β-(6-benzoyloxymethyltetrahydropyran-2-yloxy)-2,4-dichlorophenethyl]-imidazole (a) 2-Benzoyloxymethyl-3,4-dihydro-2H-pyran 9.77 g of benzoyl chloride were slowly added dropwise to a solution of 7.20 g of 2-hydroxymethyl-3,4-dihydro-2H-pyran in 14 ml of dry pyridine, whilst cooling the solution on an ice-water bath. When the addition was complete, the mixture was stirred at room temperature for 2 hours and then poured into an aqueous solution of sodium bicarbonate. The mixture was extracted with diethyl ether and the ethereal extract was washed with aqueous sodium chloride and dried over anhydrous sodium sulphate. The solvent was then evaporated off under reduced pressure and the residue was purified by distillation under reduced pressure, to give the title compound boiling at 112°–113° C./10 mmHG.

Infrared Absorption spectrum (liquid film) $v_{max}cm^{-1}$:1720, 1645, 1275.

Nuclear Magnetic Resonance Spectrum (CDCl$_3$, 60 MHz) δ ppm: 1.55–2.35 (4H, multiplet); 3.90–4.53 (3H, multiplet); 4.53–4.90 (1H, multiplet); 6.37 (1H, doublet, J=6 Hz); 7.2–8.3 (5H, multiplet).

(b) Cis- and trans-6-benzoyloxymethyl-2-[2-bromo-1-(2,4-dichlorophenyl)ethoxy]tetrahydropyran To a solution of 13.10 g of 2-benzoyloxymethyl-3,4-dihydro-2H-pyran and 13.50 g of α-bromomethyl-2,4-dichlorobenzyl alcohol in 60 ml of ether were added 2 drops of phosphorus oxytrichloride and the mixture was left to stand at room temperature for 10 days. At the end of this time, 3 drops of triethylamine were added, the solvent was evaporated off and the residue was purified by column chromatography through silica gel eluted with a 20:20:0.5 by volume mixture of hexane, benzne and ethyl acetate, to give 19.80 g of the cis-isomer and 488 mg of the trans-isomer of the title compound.

Trans-isomer

Infrared Absorption Spectrum (liquid film) $\nu_{max}$cm$^{-1}$: 1720, 1585.

Nuclear Magnetic Resonance Spectrum (CDCl$_3$, 60 MHz) δ ppm: 1.0–2.3 (6H, multiplet); 3.1–4.55 (5H, multiplet); 4.50–5.55 (2H, multiplet); 6.9–8.3 (8H, multiplet).

Cis-isomer

Infrared Absorption Spectrum (liquid film) $\nu_{max}$cm$^{-1}$: 1720, 1590, 1275.

Nuclear Magnetic Resonance Spectrum (CDCl$_3$, 60 MHz) δ ppm: 1.0–2.1 (6H, multiplet); 3.65 (2H, doublet, J=5.5 Hz); 3.35–3.95 (1H, multiplet); 4.1–4.5 (3H, multiplet); 5.5 (1H, triplet, J=5.5 Hz); 7.0–8.3 (8H, multiplet).

(c) 1-[Trans-β-(6-benzoyloxymethyltetrahydropyran-2-yloxy)-2,4-dichlorophenethyl]imidazole 8.24 g of imidazole and 12.0 g of sodium iodide were added to a solution of 19.70 g of trans-6-benzoyloxymethyl-2-[2-bromo-1-(2,4-dichlorophenyl)ethoxy]tetrahydropyran in 150 ml of dimethylformamide, and the resulting mixture was stirred on an oil bath at 130° C. for 6.5 hours. The reaction mixture was then cooled, poured into water and extracted with diethyl ether. The ethereal extract was washed with aqueous sodium chloride and dried over anhydrous sodium sulphate, after which the solvent was evaporated off. The residue was purified by column chromatography through silica gel eluted with a B 100:25:1 by volume mixture of ethyl acetate, benzene and triethylamine, to give 9.25 g of the title compound as a liquid.

Infrared Absorption Spectrum (liquid film) $\nu_{max}$cm$^{-1}$: 1720, 1590, 1500, 1475.

Nuclear Magnetic Resonance Spectrum (CDCl$_3$, 60 MHz) δ ppm: 1.1–2.0 (6H, multiplet); 2.80–4.45 (5H, multiplet); 4.52, 4.63 (together 1H, ratio about 1:1, broad singlet); 5.08–5.43 (1H, multiplet); 6.80–8.25 (11H, multiplet).

EXAMPLE 51

1-[Trans-β-(6-hydroxymethyltetrahydropyran-2-yloxy)-2,4-dichlorophenethyl]imidazole 90 ml of dioxan and 20 ml of a 25% w/v aqueous solution of sodium hydroxide were added to 9.15 g of 1-[trans-β-(6-benzoyloxymethyltetrahydropyran-2-yloxy)-2,4-dichlorophenethyl]imidazole, and the mixture was refluxed for 6 hours. At the end of this time, the reaction mixture was cooled, diluted with water and extracted with diethyl ether. The ethereal extract was washed with aqueous sodium chloride and dried over anhydrous sodium sulphate, after which the solvent was evaporated off. The residue was purified by column chromatography through silica gel eluted with a 10:20:3 by volume mixture of benzene, ethyl acetate and ethanol, to give 5.34 g of the title compound as a liquid.

Infrared Absorption Spectrum (liquid film) $\nu_{max}$cm$^{-1}$: 3350, 1590, 1500, 1465.

Nuclear Magnetic Resonance Spectrum (CDCl$_3$, 60 MHz) δ ppm: 1.0–1.9 (6H, multiplet), 2.60 (1H, singlet); 2.55–3.15 (1H, multiplet); 3.33 (2H, multiplet); 3.65–4.7 (3H, multiplet); 5.0–5.5 (1H, multiplet); 6.8–7.6 (6H, multiplet).

EXAMPLE 52

(a) 1-[Trans-β-(6-tosyloxymethyltetrahydropyran-2-yloxy)-2,4-dichlorophenethyl]imidazole A solution of 5.10 g of 1-[trans-β-(6-hydroxymethyltetrahydropyran-2-yloxy)-2,4-dichlorophenethyl]imidazole in 40 ml of dry pyridine was stirred overnight at room temperature with 2.88 g of tosyl chloride. The reaction mixture was poured into water and extracted with diethyl ether. The ethereal extract was washed with aqueous sodium chloride and dried over anhydrous sodium sulphate, and the solvent was removed by evaporation under reduced pressure. The residue was purified by column chromatography through silica gel eluted with a 20:20:1 by volume mixture of benzene, ethyl acetate and ethanol, to give 6.8 g of the title compound, as a colourless liquid.

Infrared Absorption Spectrum (liquid film) $\nu_{max}$cm$^{-1}$: 1600, 1505, 1365.

Nuclear Magnetic Resonance Spectrum (CDCl$_3$, 60 MHz) δ ppm: 0.95–1.90 (6H, multiplet), 2.43 (3H, singlet), 2.7–4.3 (5H, multiplet); 4.52 (1H, broad singlet); 4.95–5.45 (1H, multiplet); 6.8–7.95 (10H, multiplet).

(b) 1-[Cis-β-(6-tosyloxymethyltetrahydropyran-2-yloxy)-2,4-dichlorophenethyl]imidazole This was prepared in a similar manner to (a) above.

Nuclear Magnetic Resonance Spectrum (CDCl$_3$, 60 MHz) δ ppm: 1.1–2.4 (6H, multiplet); 2.46 (3H, singlet); 3.4–4.6 (5H, multiplet); 4.9–5.5 (2H, multiplet); 6.7–7.9 (10H, multiplet).

EXAMPLE 53

(a) 1-{Trans-β-[6-(4-4'-acetyl-1'-piperazinylphenoxymethyl)tetrahydropyran-2-yloxy]-2,4-dichlorophenethyl}imidazole 0.23 g of 55% sodium hydride was stirred at room temperature for 30 minutes with a solution of 0.97 g of 4-acetyl-1-(4-hydroxyphenyl)piperazine, and then 15 ml of a dimethylformamide solution containing 2.11 g of 1-[trans-β-(6-tosyloxymethyltetrahydropyran-2-yloxy)-2,4-dichlorophenethyl]imidazole and 1.20 g of sodium iodide were added to the resulting mixture. The mixture was then stirred at 80° C. for 6 hours, after which it was cooled, diluted with water and extracted with methylene chloride. The extract was washed with aqueous sodium chloride and dried over anhydrous sodium sulphate, after which the solvent was evaporated off. The residue was purified by column chromatograph through silica gel eluted with a 10:20:3 by volume mixture of benzene, ethyl acetate and ethanol, to give 1.4 g of the title compound as a colourless oil.

Infrared Absorption Spectrum (liquid film) $\nu_{max}$cm$^{-1}$: 1640, 1510, 1440.

Nuclear Magnetic Resonance Spectrum (CDCl$_3$, 60 MHz) δ ppm: 1.1–1.9 (6H, multiplet); 2.13 (3H, singlet); 2.65–3.3 (5H, multiplet); 3.35–4.4 (8H, multiplet); 4.63 (1H, broad singlet); 5.0–5.5 (1H, multiplet); 6.5–7.6 (10H, multiplet).

(b) 1-{Cis-β-[6-(4-4'-acetyl-1'-piperazinylphenoxymethyl)tetrahydropyran-2-yloxy]-2,4-dichlorophenethyl}-imidazole This was prepared in a similar manner to that described in (a) above.

Nuclear Magnetic Resonance Spectrum (CDCl$_3$, 60 Mhz) δ ppm: 1.15–2.40 (6H, multiplet); 2.13 (3H, singlet); 2.75–3.25 (4H, multiplet); 3.3–4.8 (10H, multiplet); 5.1–5.5 (1H, multiplet); 6.7–7.9 (10H, multiplet).

EXAMPLE 54

1-{Trans-β-[6-(4-4'-acetyl-1'-piperazinyl-2-chlorobenzyloxymethyl)tetrahydropyran-2-yloxy]-2,4-dichlorophenethyl}imidazole A solution of 1.12 g of 4-(4-acetyl-1-piperazinyl)-2-chlorobenzyl alcohol in 10 ml of dry dimethylformamide was stirred at room temperature for 30 minutes with 0.22 g of 50% sodium hydride. At the end of this time, 10 ml of a dimethylformamide solution containing 2.0 g of 1-[trans-β-(6-tosyloxymethyltetrahydropyran-2-yloxy)-2,4-dichlorophenethyl]imidazole and 0.57 g of sodium iodide were added to the mixture, which was then heated at 80°–90° C. for 10 hours. The mixture was then cooled, diluted with water and extracted with methylene chloride. The extract was washed with aqueous sodium chloride and dried over anhydrous sodium sulphate, after which the solvent was evaporated off and the residue was purified by column chromatography through silica gel eluted with a 20:20:1 by volume mixture of benzene, ethyl acetate and ethanol, to give 838 mg of the title compound, as a pale brown liquid.

Infrared Absorption Spectrum (liquid film) $\nu_{max}$cm$^{-1}$: 1640, 1610, 1500, 1440.

Nuclear Magnetic Resonance Spectrum (CDCl$_3$, 60 MHz) δ ppm: 0.8–2.0 (6H, multiplet); 2.13 (3H, singlet); 2.8–4.8 (16H, multiplet); 5.0–5.5 (1H, multiplet); 6.5–7.6 (9H, multiplet).

EXAMPLE 55

1-{Trans-β-[6-(4-4'-benzoyl-1'-piperazinyl-2-chlorobenzyloxymethyl)tetrahydropyran-2-yloxy]-2,4-dichlorophenethyl}imidazole A solution of 1.0 g of 4-(4-benzoyl-1-piperazinyl)-2-chlorobenzyl alcohol in 5 ml of dry dimethylformamide was stirred at room temperature for 30 minutes with 0.16 g of 55% sodium hydride, and then 10 ml of a dimethylformamide solution containing 1.44 g of 1-[trans-(6-tosyloxymethyltetrahydropyran-2-yloxy)-2,4-dichlorophenethyl]imidazole and 0.21 g of sodium iodide were added to the mixture. The mixture was then heated, with stirring, at 75° C. for 7 hours and then at 85° C. for a further 7 hours. The mixture was then cooled, water was added and the mixture was extracted with methylene chloride. The extract was washed with aqueous sodium chloride and dried over anhydrous sodium sulphate, after which the solvent was evaporated off. The resulting residue was purified by column chromatography through silica gel eluted with a 20:20:1 by volume mixture of benzene, ethyl acetate and ethanol, to give 1.112 g of the title compound as a colorless oil.

Infrared Absorption Spectrum (liquid film) $\nu_{max}$cm$^{-1}$: 1675, 1625, 1610, 1500, 1435.

Nuclear Magnetic Resonance Spectrum (CDCl$_3$, 60 MHz) δ ppm: 1.1–1.9 (6H, multiplet); 2.95–4.8 (16H, multiplet); 5.0–5.5 (1H, multiplet); 6.65–7.7 (14H, multiplet).

EXAMPLE 56

1-{3-(4-fluorophenyl)-trans-3-[6-(4-fluorophenoxymethyl)tetrahydropyran-2-yloxy]propyl}imidazole (a) Trans-6-(4-fluorophenoxymethyl)-2-[3-chloro-1-(4-fluorophenyl)propoxy]tetrahydropyran One drop of phosphorus oxytrichloride was added to a solution of 222 mg of 3-chloro-1-(4-fluorophenyl)-propanol and 233 mg of 2-(4-fluorophenoxymethyl)-3,4-dihydro-2H-pyran in 5 ml of diethyl ether, and the mixture was stirred at room temperature for 2 days. At the end of this time, 2 drops of triethylamine were added, the solvent was evaporated off and the residue was purified by column chromatography through silica gel, to give 245 mg of the title compound.

Infrared Absorption Spectrum (liquid film) $\nu_{max}$cm$^{-1}$: 1605, 1505, 1470, 1440.

Nuclear Magnetic Resonance Spectrum (CDCl$_3$, 60 MHz) δ ppm: 0.93–1.93 (6H, multiplet); 1.93–2.37 (2H, two triplets); 3.12–5.13 (7H, multiplet); 6.5–7.5 (8H, multiplet).

(b) 1-{3-(4-Fluorophenyl)-trans-3-[6-(4-fluorophenoxymethyl)tetrahydropyran-2-yloxy]propyl}-imidazole A mixture of 56 mg of imidazole and 36 mg of 55% sodium hydride was stirred in 2 ml of dimethylformamide at 60°–70° C. for 30 minutes. The mixture was left to cool at room temperature, and then a solution of 218 mg of trans-6-(4-fluorophenoxymethyl)-2-[3-chloro-1-(4-fluorophenyl)propoxy]tetrahydropyran in 1 ml of dimethylformamide was added, and the mixture was heated, with stirring, at 80°–90° C. for 6 hours. At the end of this time, the mixture was treated and the product purified essentially as described in Example 34(b)(i), to give 110 mg of the title compound.

Infrared Absorption Spectrum (liquid film) $\nu_{max}$cm$^{-1}$: 1605, 1510, 1455.

Nuclear Magnetic Resonance Spectrum (CDCl$_3$, 60 MHz) δ ppm: 1.14–2.45 (8H, multiplet); 3.45–4.90 (7H, multiplet); 6.72–7.65 (11H, multiplet).

EXAMPLE 57

1-{3-(4-Fluorophenyl)-trans-3-[6-(4-acetamidophenoxymethyl)tetrahydropyran-2-yloxy]propyl}imidazole (a) 2-(4-Acetamidophenoxymethyl)-3,4-dihydro-2H-pyran A solution of 831 mg of 4-acetamidophenol in 5 ml of dimethylformamide was stirred for 30 minutes at room temperature with 240 mg of 55% sodium hydride. 1.34 g of 2-tosyloxymethyl-3,4-dihydro-2H-pyran was then added and the mixture was heated, with stirring, at 90°–95° C. for 4.5 hours. The mixture was then poured into water and extracted with diethyl ether. The ethereal extract was washed with water and dried over anhydrous magnesium sulphate, after which the solvent was evaporated off. The residue was purified by column chromatography through silica gel, to give 965 mg of the title compound, melting at 114°–116° C.

(b) Trans-6-(4-acetamidophenoxymethyl)-2-[3-chloro-1-(4-fluorophenyl)propoxy]tetrahydropyran A catalytic amount (2 drops) of phosphorus oxytrichloride was added to 10 ml of an ethereal solution containing 277 mg of 3-chloro-1-(4-fluorophenyl)-propanol and 330 mg of 2-(4-acetamidophenoxymethyl)-3,4-dihydro-2H-pyran and the mixture was allowed to react at room temperature for 8 days. The precipitated crystals were separated by filtration, giving 240 mg of the isomer of lesser polarity of the title compound, melting at 133°–135° C.

3 Drops of triethylamine were then added to the filtrate, after which the solvent was evaporated off. The residue was purified by column chromatography through silica gel, giving an approximately 3:7 mixture of the isomers of lesser and greater polarity of the title compound.

Isomer of Lesser Polarity

Infrared Absorption Spectrum (KBr) $\nu_{max}$cm$^{-1}$: 3250, 1665, 1605, 1550, 1515.

Nuclear Magnetic Resonance Spectrum (deuterodimethylformamide, 60 MHz) δ ppm: 1.35–2.6 (8H, multiplet); 2.05 (3H, singlet); 3.35–4.3 (5H, multiplet); 4.57 (1H, singlet); 4.93 (1H, doublet of doublets, J=6 and 8 Hz); 6.65–7.75 (9H, multiplet).

Mixture of Isomers of Lesser and Greater Polarity

Infrared Absorption Spectrum (liquid film) $\nu_{max}$cm$^{-1}$: 3310, 1670, 1545, 1510.

Nuclear Magnetic Resonance Spectrum (CDCl$_3$, 60 MHz) δ ppm: 1.0–2.3 (11H, multiplet); 3.0–5.2 (7H, multiplet); 6.4–7.5 (9H, multiplet); 7.5–8.3 (1H, broad singlet).

(c) 1-{3-(4-Fluorophenyl)-trans-3-[6-(4-acetamidophenoxymethyl)tetrahydropyran-2-yloxy]propyl}-imidazole (i) Isomer of Lesser Polarity A solution of 39 mg of imidazole in 3 ml of dimethylformamide was stirred for 30 minutes at 80° C. with 25 mg of 55% sodium hydride, and then 210 mg of the isomer of lesser polarity of trans-6-(4-acetamidophenoxymethyl)-2-[3-chloro-1-(4-fluorophenyl)propoxy]tetrahydropyran and 87 mg of sodium iodide were added, and the mixture was stirred at 90°–95° C. for 5 hours. The mixture was then treated and the product purified essentially as described in Example 34(b)(i), to give 212 mg of the title compound.

Infrared Absorption Spectrum (liquid film) $\nu_{max}$cm$^{-1}$: 3250, 1660, 1600, 1540, 1510.

Nuclear Magnetic Resonance Spectrum (CDCl$_3$, 60 MHz) δ ppm: 1.25–2.4 (8H, multiplet); 2.10 (3H, singlet); 3.65–4.3 (5H, multiplet); 4.4–4.8 (2H, multiplet); 6.6–7.65 (11H, multiplet); 8.77 (1H, broad singlet).

(ii) Mixture of Isomers of Lesser and Greater Polarity

A solution of 52 mg of imidazole in 5 ml of dimethylformamide was stirred for 30 minutes at 80° C. with 34 mg of 55% sodium hydride, and then 280 mg of a mixture of the isomers of lesser and greater polarity of trans-6-(4-acetamidophenoxymethyl)-2-[3-chloro-1-(4-fluorophenyl)propoxy]tetrahydropyran and 116 mg of sodium iodide were added, after which the mixture was stirred at 90° C. for 5 hours. The mixture was then treated and the product purified essentially as described in Example 34(b)(i), to give 259 mg of the title compound.

Infrared Absorption Spectrum (liquid film) $\nu_{max}$cm$^{-1}$: 3250, 1660, 1600, 1540, 1510.

Nuclear Magnetic Resonance Spectrum (CDCl$_3$, 60 MHz) δ ppm 1.2–2.4 (8H, multiplet); 2.10 (3H, singlet); 3.1–5.1 (7H, multiplet); 6.5–7.6 (11H, multiplet); 8.92, 9.03 (together 1H, broad singlet).

PREPARATION

The following illustrates the preparation of one of the starting materials used in the foregoing Examples.

2-Tosyloxymethyl-3,4-dihydro-2H-pyran

Whilst cooling a solution of 14.2 g of 2-hydroxymethyl-3,4-dihydro-2H-pyran in 120 ml of pyridine on an ice-water bath at 0°–5° C., 28.4 g of crystals of tosyl chloride were added and the mixture was then stirred at room temperature overnight. The salt which precipitated with the aid of a Celite (Trademark) filter aid was separated by filtration and the filtrate was concentrated under reduced pressure. Water was added to the residue and the resulting mixture was extracted with diethyl ether. The ethereal extract was washed with a saturated aqueous solution of sodium bicarbonate and then with aqueous sodium chloride, after which the solvent was evaporated off under reduced pressure. The residue was purified by column chromatography through silica gel eluted with a 7:1 by volume mixture of hexane and ethyl acetate, to give 31.5 g of the title compound, in the form of colourless crystals melting at 47°–48° C.

ANTI-FUNGAL ACTIVITY

Each test compound was dissolved in acetone or in water to prepare a 5% w/v solution. These solutions were each subjected to continuous two-step dilutions with sterilized water and thereafter each solution, in an amount of 1 ml, was placed in a separate Petri dish, to which 9 ml of sterilized Sabouraud's agar medium was added. After stirring the mixture sufficiently, it was solidified to prepare a flat agar plate. Each of the microorganisms listed in the following Table was then inoculated onto a plate with a platinum wire and then cultivated at 27° C. for 3 days for yeast-like microorganisms and for 5 days for hyphomycetic microorganisms. At the end of this time, the growth of the microorganism was judged by the naked eye to determine the minimal inhibitory concentration (μg/ml). The results are shown in the following Table, in which the microorganisms employed are identified by the following abbreviations:

NA = *Nocardia asteroides*;
CA = *Candida albicans*;
CT = *Candida tropicalis*;
CN = *Cryptococcus neoformans*; and
TI = *Trychophyton interdigitale*;

and the test compounds employed are identified by the following symbols:

A. Trans-1-[6-(2,4-dichlorobenzyloxy)tetrahydropyran-2-ylmethyl]imidazole;

B. Trans-1-[6-(2,4-dichlorobenzyloxy)tetrahydropyran-2-ylmethyl]-1H-1,2,4-triazole;

C: Trans-1-{6-[α-(4-fluorobenzyl)-4-chlorobenzyloxy]tetrahydropyran-2-ylmethyl}imidazole;

D: Trans-1-{6-[α-(2,4-dichlorobenzyl)benzyloxy]tetrahydropyran-2-ylmethyl}imidazole;

E: Trans-1-{6-[α-(2-thienyl)-2,4-dichlorophenethyloxy]tetrahydropyran-2-ylmethyl}imidazole;

F: Trans-1-{6-[α-(2-thienyl)-2,4-dichlorophenethyloxy]tetrahydropyran-2-ylmethyl}imidazole;

G: 1-{Trans-β-[6-(2,4-dichlorobenzyloxy)tetrahydropyran-2-ylmethoxy]-4-chlorophenethyl}imidazole;

H: 1-{Trans-β-[6-(2,4-dichlorobenzyloxy)tetrahydropyran-2-ylmethoxy]-2,4-dichlorophenethyl}imidazole;

I: Isomer of greater polarity of 1-{trans-β-[6-(2,4-dichlorophenoxymethyl)tetrahydropyran-2-yloxy]-4-chlorophenethyl}imidazole;

J: Isomer of lesser polarity of 1-{trans-β-[6-(4-fluorophenoxymethyl)tetrahydropyran-2-yloxy]-2,4-dichlorophenethyl≡imidazole;

K: Isomer of lesser polarity of 1-{trans-β-[6-(4-chlorobenzylthiomethyl)tetrahydropyran-2-yloxy]-2,4-dichlorophenethyl}imidazole;

L: Mixture of isomers of lesser and greater polarity of 1-{trans-β-[6-(4-phenylphenoxymethyl)tetrahydropyran-2-yloxy]-2,4-dichlorophenethyl}imidazole;

M: Isomer of lesser polarity of 1-{trans-β-[6-(4-fluorophenoxymethyl)tetrahydropyran-2-yloxy]-4-chlorophenethyl}imidazole;

N: Mixture of isomers of lesser and greater polarity of 1-{4-(4-chlorophenyl)-trans-2-[6-(2,4-dichlorophenoxymethyl)tetrahydropyran-2-yloxy]-2-butoxy}imidazole;

O: Mixture of isomers of lesser and greater polarity of 1-{trans-β-[6-(4-4'-acetyl-1'-piperazinylphenoxymethyl)tetrahydropyran-2-yloxy]-2,4-dichlorophenethyl}imidazole;

P: Mixture of isomers of lesser and greater polarity of 1-{trans-β-[6-(4-4'-acetyl-1'-piperazinyl-2-chlorobenzyloxymethyl)tetrahydropyran-2-yloxy]-2,4-dichlorophenethyl}imidazole.

TABLE

| Test Compound | Microorganism | | | | |
|---|---|---|---|---|---|
| | NA | CA | CT | CN | TI |
| A | 6.25 | 100 | 50 | 100 | 6.25 |
| B | 12.5 | 100 | 100 | 100 | 12.5 |
| C | 3.13 | 12.5 | 12.5 | 12.5 | 25 |
| D | 0.78 | 25 | 6.25 | 1.56 | 12.5 |
| E | 0.78 | 12.5 | 6.25 | 6.25 | 12.5 |
| F | 1.56 | 50 | 3.13 | 6.25 | 6.25 |
| G | 0.39 | 100 | 3.13 | 3.13 | 12.5 |
| H | 0.78 | >100 | 1.56 | 3.13 | 6.25 |
| I | 0.39 | 12.5 | 3.13 | 1.56 | 50 |
| J | 0.78 | 50 | 3.13 | 6.25 | 6.25 |
| K | 1.56 | 100 | 6.25 | 12.5 | 12.5 |
| L | 0.78 | >100 | 3.13 | 3.13 | 50 |
| M | 3.13 | 6.25 | 12.5 | 3.13 | 50 |
| N | 0.78 | 12.5 | 6.25 | 3.13 | >100 |
| O | 6.25 | 50 | 100 | 50 | >100 |
| P | 3.13 | 50 | 25 | 6.25 | >100 |

We claim:

1. A compound of the formula (I):

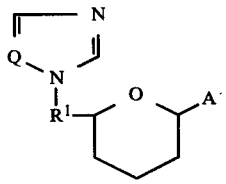

(I)

wherein:
Q represents a =CH— group;
$R^1$ is methylene; and
A is —$OR^2$
wherein $R^2$ represents a $C_1$–$C_6$ alkyl group; a $C_2$–$C_6$ alkenyl group; a $C_2$–$C_6$ alkynyl group; a phenyl group; a phenyl group substituted with up to three halogen atoms, a $C_1$–$C_6$ alkyl group or a $C_1$–$C_6$ alkoxy group;
or a group of formula

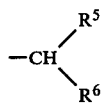

in which $R^5$ represents a hydrogen atom; a $C_1$–$C_6$ alkyl group; a phenyl group; a phenyl group substituted with up to two halogen atoms, a $C_1$–$C_6$ alkyl group or a $C_1$–$C_6$ alkoxy group; a thienyl group; a thienyl group substituted with a halogen atom; a furyl group; or a furyl group substituted with a halogen atom; $R^6$ represents a phenyl group; a phenyl group substituted with up to three halogen atoms, a $C_1$–$C_6$ alkyl group, a $C_1$–$C_6$ alkoxy group, a nitro group, a phenoxy group, or a phenyl group; a benzyl group; a benzyl group substituted on the benzene ring with up to two halogen atoms, a $C_1$–$C_6$ alkyl group, or a $C_1$–$C_6$ alkoxy group; a thienyl group; a thienyl group substituted with a halogen atom; a furyl group; or a furyl group substituted with a halogen atom; or an acid addition salt or the cupric chloride, zinc chloride or stannous chloride complex thereof.

2. The compound of claim 1 in which $R^2$ represents a group of the formula

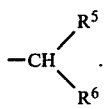

3. The compound of claim 2, in which $R^5$ represents a hydrogen atom; a $C_1$–$C_6$ alkyl group; a phenyl group; a phenyl group substituted with up to two halogen atoms; a thienyl group; or a thienyl group substituted with a halogen atom and $R^6$ represents a phenyl group; a phenyl group substituted with up to two halogen atoms; a benzyl group; or a benzyl group substituted with up to two halogen atoms.

4. The compound of claim 2, in which $R^5$ represents a hydrogen atom; a phenyl group; or a phenyl group substituted with up to two halogen atoms and $R^6$ represents a phenyl group; or a phenyl group substituted with up to two halogen atoms.

5. The compound of claim 2, in which $R^5$ represents a phenyl group; a thienyl group; a phenyl group substituted with up to two halogen atoms; or a thienyl group substituted with a halogen atom and $R^6$ represents a benzyl group or a benzyl group substituted with up to two halogen atoms.

6. The compound of claim 1, in the trans configuration with respect to the tetrahydropyran ring.

7. The compound of claim 1:
1-[6-(2,4-dichlorobenzyloxy)tetrahydropyran-2-ylmethyl]imidazole
or an acid addition salt or the cupric chloride, zinc chloride or stannous chloride complex thereof.

8. The compound of claim 1:
1-{6[α-(4-fluorobenzyl)-4-chlorobenzyloxy]tetrahydropyran-2-ylmethyl}imidazole or an acid addition salt or the cupric chloride, zinc chloride or stannous chloride complex thereof.

9. The compound of claim 1:
1-{6-[α-(2,4-dichlorobenzyl)benzyloxy]tetrahydropyran-2-ylmethyl}imidazole or an acid addition salt or the cupric chloride, zinc chloride or stannous chloride complex thereof.

10. The compound of claim 1:
1-{6-[α-(2,4-dichlorobenzyl)-4-fluorobenzyloxy]tetrahydropyran-2-ylmethyl}imidazole or an acid addition salt or the cupric chloride, zinc chloride or stannous chloride complex thereof.

11. The compound of claim 1:
1-[6-(2,4-dichloro-α-2'-thienylphenethyloxy)tetrahydropyran-2-ylmethyl]imidazole or an acid addition salt or the cupric chloride, zinc chloride or stannous chloride complex thereof.

12. The compound of claim 7, in the trans configuration with respect to the tetrahydropyran ring.

13. The compound of claim 8, in the trans configuration with respect to the tetrahydropyran ring.

14. The compound of claim 9, in the trans configuration with respect to the tetrahydropyran ring.

15. The compound of claim 10, in the trans configuration with respect to the tetrahydropyran ring.

16. The compound of claim 11, in the trans configuration with respect to the tetrahydropyran ring.

17. An antimicrobial composition comprising an antimicrobial effective amount of an antimicrobial agent and a carrier or diluent, wherein the antimicrobial agent is selected from a compound of formula (I):

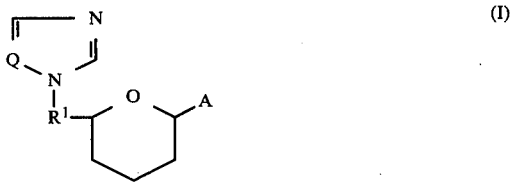

wherein:
Q represents a =CH— group;
$R^1$ is methylene; and
A is —$OR^2$
wherein $R^2$ represents a $C_1$-$C_6$ alkyl group; a $C_2$-$C_6$ alkenyl group; a $C_2$-$C_6$ alkynyl group; a phenyl group; a phenyl group substituted with up to three halogen atoms, a $C_1$-$C_6$ alkyl group or a $C_1$-$C_6$ alkoxy group;
or a group of formula

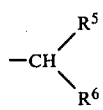

in which $R^5$ represents a hydrogen atom; a $C_1$-$C_6$ alkyl group; a pheny group; a phenyl group substituted with up to two halogen atoms, a $C_1$-$C_6$ alkyl group or a $C_1$-$C_6$ alkoxy group; a thienyl group; a thienyl group substituted with a halogen atom; a furyl group; or a furyl group substituted with a halogen atom; $R^6$ represents a phenyl group; a phenyl group substituted with up to three halogen atoms, a $C_1$-$C_6$ alkyl group, a $C_1$-$C_6$ alkoxy group, a nitro group, a phenoxy group, or a phenyl group; a benzyl group; a benzyl group substituted on the benzene ring with up to two halogen atoms, a $C_1$-$C_6$ alkyl group, or a $C_1$-$C_6$ alkoxy group; a thienyl group; a thienyl group substituted with a halogen atom; a furyl group; or a furyl group substituted with a halogen atom; or an acid addition salt or the cupric chloride, zinc chloride or stannous chloride complex thereof.

18. The composition of claim 17, in which $R^2$ represents a group of formula

19. The composition of claim 18, in which $R^5$ represents a hydrogen atom; a $C_1$-$C_6$ alkyl group; a phenyl group; a phenyl group substituted with up to two halogen atoms; a thienyl group; or a thienyl group substituted with a halogen atom and $R^6$ represents a phenyl group; a phenyl group substituted with up to two halogen atoms; a benzyl group; or a benzyl group substituted with up to two halogen atoms.

20. The composition of claim 18, in which $R^5$ represents a hydrogen atom; a phenyl group; or a phenyl group substituted with up to two halogen atoms and $R^6$ represents a phenyl group; or a phenyl group substituted with up to two halogen atoms.

21. The composition of claim 18, in which $R^5$ represents a phenyl group; a thienyl group; a phenyl group substituted with up to two halogen atoms; or a thienyl group substituted with a halogen atom and $R^6$ represents a benzyl group or a benzyl group substituted with up to two halogen atoms.

22. A composition as claimed in claim 17, wherein said compound is in the trans configuration with respect to the tetrahydropyran ring.

23. The composition of claim 17, wherein said agent is selected from the group consisting of:
1-[6-(2,4-dichlorobenzyloxy)tetrahydropyran-2-ylmethyl]imidazole
1-{6-[α-(4-fluorobenzyl)-4-chlorobenzyloxy]tetrahydropyran-2-ylmethyl}imidazole
1-{6-[α-(2,4-dichlorobenzyl)benzyloxy]tetrahydropyran-2-ylmethyl}imidazole
1-{6-[α-(2,4-dichlorobenzyl)-4-fluorobenzyloxy]tetrahydropyran-2-ylmethyl}imidazole
1-[6-(2,4-dichloro-α-2'-thienylphenethyloxy)tetrahydropyran-2-ylmethyl]imidazole
or an acid addition salt or the cupric chloride, zinc chloride or stannous chloride complex thereof.

24. The composition of claim 23, wherein the compound is in the trans configuration with respect to the tetrahydropyran ring.

* * * * *